US008592569B2

(12) United States Patent
Inoue et al.

(10) Patent No.: US 8,592,569 B2
(45) Date of Patent: Nov. 26, 2013

(54) SMALL RNA-DEPENDENT TRANSLATIONAL REGULATORY SYSTEM IN CELL OR ARTIFICIAL CELL MODEL

(75) Inventors: Tan Inoue, Kyoto (JP); Hirohide Saito, Kyoto (JP); Yusho Kato, Hyogo (JP); Kenichi Yoshikawa, Kyoto (JP); Ayako Yamada, Paris (FR); Toru Yamanaka, Hyogo (JP)

(73) Assignee: Japan Science and Technology Agency, Saitama (JP)

( * ) Notice: Subject to any disclaimer, the term of this patent is extended or adjusted under 35 U.S.C. 154(b) by 92 days.

(21) Appl. No.: 12/743,908

(22) PCT Filed: Nov. 21, 2008

(86) PCT No.: PCT/JP2008/071214

§ 371 (c)(1), (2), (4) Date: Aug. 31, 2010

(87) PCT Pub. No.: WO2009/066758

PCT Pub. Date: May 28, 2009

(65) Prior Publication Data

US 2010/0323356 A1 Dec. 23, 2010

(30) Foreign Application Priority Data

Nov. 22, 2007 (JP) ................................ 2007-303661

(51) Int. Cl.
*C07H 21/04* (2006.01)

(52) U.S. Cl.
USPC ........................................................ 536/24.5

(58) Field of Classification Search
USPC ........................................................ 536/24.5
See application file for complete search history.

(56) References Cited

U.S. PATENT DOCUMENTS

| | | | | |
|---|---|---|---|---|
| 6,428,971 | B1 * | 8/2002 | Shinabarger et al. | 435/15 |
| 2002/0169306 | A1 * | 11/2002 | Kitazato et al. | 536/23.4 |
| 2006/0063232 | A1 * | 3/2006 | Grabherr et al. | 435/69.1 |
| 2007/0136827 | A1 * | 6/2007 | Collins et al. | 800/14 |

FOREIGN PATENT DOCUMENTS

JP 2005-341865 12/2005

OTHER PUBLICATIONS

MHS2007 & Micro-Nano COE Final Conference Program, 2007 International Symposium on Micro-NanoMechatronics and Human Science, Nov. 11-14, 2007, Nagoya, Japan, pp. 1-16.*

Bauer et al., "Engineered riboswitches as novel tools in molecular biology," J. Biotechnol. 124(1):4-11 (2006).

Davidson et al., "Synthetic RNA circuits," Nature Chem. Biology 3(1):23-8 (2007).

Isaacs et al., "Engineered riboregulators enable post-transcriptional control of gene expression," Nature Biotechnol. 22(7):841-7 (2004).

Repoila et al., "Small non-coding RNAs, co-ordinators of adaptation processes in *Escherichia coli*: the Rpos paradigm," Mol. Microbiol. 48(4):855-61 (2003).

Extended European Search Report and Written Opinion mailed on Jan. 24, 2011 in related European Application No. EP08852782.5.

Altuvia, Shoshy, et al., The *Escherichia coli* OxyS regulatory RNA represses fhla translation by blocking ribosome binding, The EMBO Journal, 1998, vol. 17, No. 20, p. 6069-6075.

Chen, Guangnan, et al., Features of a Leader Peptide Coding Region that Regulate Translation Initiation for the Anti-Trap Protein of *B. subtilis*, Molecular Cell, 2004, vol. 13, p. 703-711.

Isaacs, Farren J., et al., Engineered riboregulators enable post-transcriptional control of gene expression, Nature Biotechnology, Jul. 2004, vol. 22, No. 7, p. 841-847.

Isaacs, Farren, et al., RNA synthetic biology, Nature Biotechnology, May 2006, vol. 24, No. 5, p. 545-554.

Ishikawa, Keitaro, et al., Expression of a cascading genetic network within liposomes, FEBS, Sep. 2004, p. 387-390.

Kashida, Shunichi, et al., Jinko RNA to RNAI Mochiita Hito Saibo deno Hon'yaku Seigyo System, Dai 9 Kai Nippon RNS Gakkai Nenkai (Dai 9 Kai RNA Meeting) Yoshishu, Jul. 28, 2007, p. 199, P-53.

Noireaux, Vincent, et al., A vesicle bioreactor as a step toward an artificial cell assembly, Procedures National Academy Science, 2004, vol. 101, No. 51, p. 17669-17674.

Nomura, Shin-ichiro, et al., Gene Expression within Cell-Sized Lipid Vesicles, ChemBioChem, 2003, 4 (11), p. 1172-1175.

Saito, Hirohide and T. Inoue, et al., RNA and RNP as new molecular parts in synthetic biology, J. of Biotechnology, 2007, vol. 132, p. 1-7.

Sharma, Cynthia M., et al. A small RNA regulates multiple ABC transporter mRNAs by targeting C/A-rich elements inside and upstream of ribosome-binding sites, Gene & Development, Nov. 2007, vol. 21, p. 2804-2817.

International Search Report mailed Feb. 24, 2009 in related International application No. PCT/JP2008/071214.

(Continued)

*Primary Examiner* — Brian Whiteman

(74) *Attorney, Agent, or Firm* — Meunier Carlin & Curfman, LLC

(57) ABSTRACT

An object of the present invention is to construct an mRNA which specifically responds to a short RNA sequence and can activate, repress, and regulate the translation of the desired gene, and to construct an artificial cell model system using a liposome comprising the mRNA and a cell-free translational system encapsulated therein. The present invention provides: an mRNA comprising a target RNA-binding site located immediately 5' to the ribosome-binding site, and a nucleotide sequence located 5' to the target RNA-binding site, the nucleotide sequence being complementary to the ribosome-binding site; an mRNA comprising a small RNA-binding site located 3' to the start codon, and a nucleotide sequence located 3' to the small RNA-binding site, the nucleotide sequence encoding a protein; and a liposome comprising any of these mRNAs encapsulated therein.

6 Claims, 16 Drawing Sheets

(56) References Cited

OTHER PUBLICATIONS

Saito H, et al. "Towards Constructing Synthetic Cells: RNA/RNP Evolution and Cell-Free Translational Systems in Giant Liposomes," Micro-Nanomechatronics and Human Science, 2007. MHS '07. International Symposium on. Nov. 12, 2007, pp. 286-291.

Baker, CS., et al., CsrA inhibits translation initiation of *Escherichia coli* hfq by binding to a single site overlapping the Shine-Dalgarno sequence, J. Bacteriology, Aug. 2007, vol. 189, No. 15, p. 5472-5481.

Caban, et al., "The L7Ae RNA binding motif is a multifunctional domain required for the ribosome-dependent Sec incorporation activity of Sec insertion sequence binding protein 2," Mol. Cell. Biol. 27(18):6350-60 (2007).

Caillet, et al., "The modular structure of *Escherichia coli* threonyl-tRNA synthetase as both an enzyme and a regulator of gene expression," Mol. Microbiol. 47(4):961-74 (2003).

Edwards, et al., "Riboswitches: small-molecule recognition by gene regulatory RNAs," Curr. Opin. Struct. Biol. 17(3):273-9 (2007).

Ptashne, M., "Regulation of Transcription: from lambda to eukaryotes," Trends in Biochemical Sciences, 30 (6):275-279 (2005).

Winkler et al., "Regulation of bacterial gene expression by riboswitches," Ann. Rev. Microbiol. 59:487-517 (2005).

International Search Report, mailed Dec. 16, 2008 in related International application No. PCT/JP2008/071213.

Hara, Tomoaki, et al., RNP Motif L7Ae/BoxC/D o Riyo shita Tanpakushitsu Oto Hon'Yaku Seigyo System no Kochiku, Dai 10 Kai the RNA Society of Japan Nenkai Yoshishu, Jul. 23, 2008, p. 141 (P-41).

Kobayashi Tetsuhiro, et al., RNP Motif o Riyo shita Tanpakushitsu Oto Hon'yaku Seigyo System no Kochiku, 30th Annual Meeting of the Molecular Biology Society of Japan, Dai 80 Kai The Japanese Biochemical Society Taikai Godo Taikai Koen Yoshishu, Nov. 25, 2007, p. 879 (4P-1323).

* cited by examiner

FIG.3(A) 5′-UGGAGAAGCAGGGCACGUGCA-3′

FIG.13
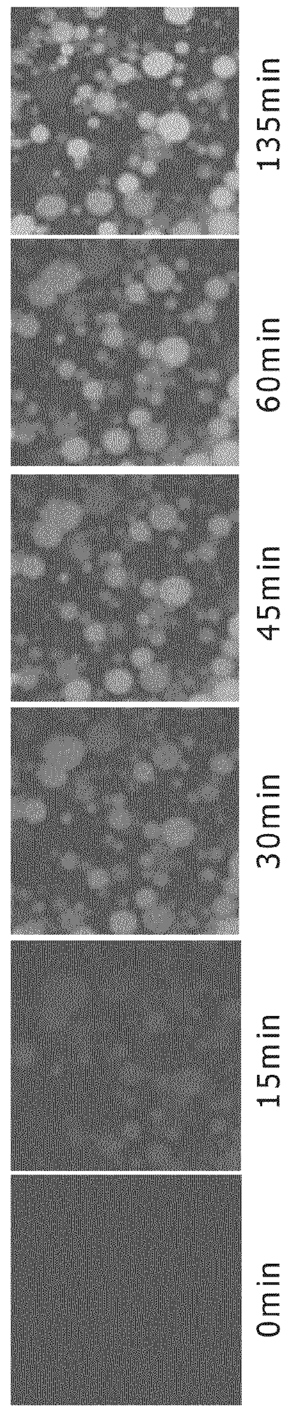
FIG.14(A)
FIG.14(B)
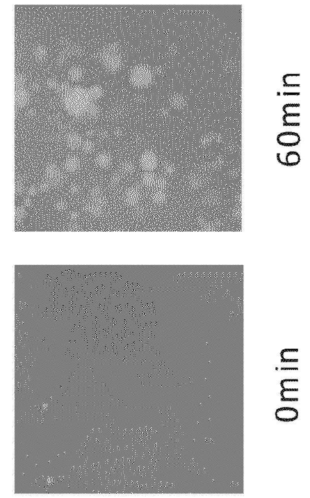

SMALL RNA-DEPENDENT TRANSLATIONAL REGULATORY SYSTEM IN CELL OR ARTIFICIAL CELL MODEL

TECHNICAL FIELD

The present invention relates to a translational regulatory system in a cell or an artificial cell model.

BACKGROUND ART

With the progress of RNA structural biology, it has been increasing evident in recent years that in vivo complicated RNA molecules are composed of accumulated RNA modules, which can be divided physically into functional units. The effectiveness of modular engineering has already been demonstrated in such a way that: an artificial functional RNA molecule has been constructed by a method which involves combining a plurality of naturally occurring RNA modules; and further, an artificial ribozyme has been developed successfully using the in vitro selection method.

On the other hand, there are naturally occurring riboswitches which have metabolite (e.g., amino acids or nucleic acids)-binding RNA modules on mRNAs and regulate gene expression in a metabolite concentration-dependent manner. Specifically, riboswitches are known, such as adenine riboswitches, glycine riboswitches, and SAM riboswitches. It has been revealed that these riboswitches regulate the interaction between the SD sequence/start codon and the ribosome associated with ligand binding-induced structural change in mRNA or regulate terminator structures.

Moreover, it has been increasing evident in recent years that small RNA molecules such as micro-RNAs play an important role in the development, differentiation, canceration, etc., of cells. The expression of these small RNA molecules dynamically varies depending on cell states or intracellular localization. Thus, it has been expected to develop a technique of detecting the expression of these small RNA molecules and detecting cells according to the expression levels, or a technique of regulating the fate of cells according to the expression levels.

Heretofore, a biosensor is known, which uses a nucleic acid probe for detecting a target nucleic acid, wherein the nucleic acid probe uses HIV DNA as a substrate and is structurally changed upon hybridization to the target nucleic acid to form an intracellular hybridization site and a stem moiety containing a self nucleic acid enzyme (see Patent Document 1). This technique is aimed at developing a biosensor and is not aimed at constructing an artificial information conversion system which converts an arbitrary input factor (e.g., miRNA) to an arbitrary output (e.g., GFP). Furthermore, in this technique, the effect of responsiveness to RNA substrates such as miRNAs is unknown, because the substrate used is DNA.

A technique of regulating translation reaction within *E. coli* using an artificial RNA is also known (see Non-Patent Document 1). However, this technique is a system intracellularly constructed in advance. Therefore, the possibility cannot be denied that other factors participate in the translational regulation. Moreover, the optimal concentrations of a substrate RNA and the artificial RNA cannot be adjusted strictly.

A technique of encapsulating a DNA or mRNA together with a cell-free translational system into liposomes prepared by natural swelling is known (see Non-Patent Documents 2 and 3). However, of all the liposome prepared by natural swelling, only approximately 10% actually promoted translation reaction, and it was difficult to promote translation reaction within all the liposomes.

On the other hand, it has been reported recently that a cell-free translational system is expressed within liposomes prepared from an emulsion, which is a micrometer-scale cell-sized droplet (see Non-Patent Document 4). However, this method requires the procedure of collecting the liposomes by centrifugation and therefore hardly performs the simultaneous real-time monitoring of translation within a plurality of liposomes. Moreover, the conventional technique used a translational system based on cell extracts and therefore, could not exclude the influence of unknown factors.

Furthermore, intraliposomal translational regulation has not been developed so far.

Patent Document 1: Japanese Patent Publication No. 2005-341865

Non-Patent Document 1: Isaacs F J et al; Nat Biotechnol., 22 (7): 841-7, 2004

Non-Patent Document 2: Ishikawa K et al; FEBS Lett., 576 (3): 387-90, 2004

Non-Patent Document 3: Nomura S M et al; Chembiochem., 4 (11): 1172-5, 2003 Gene expression within cell-sized lipid vesicles Non-Patent Document 4: Vincent Noireaux et al; Proc Natl Acad Sci USA., 101 (51): 17669-74, 2004

DISCLOSURE OF THE INVENTION

Problems to be Solved by the Invention

An object of the present invention is: to construct an mRNA which responds to the desired molecule and can activate the translation of the desired gene; to construct an artificial information conversion system which converts arbitrary input information to the output of a target protein; and to construct a translational regulatory system in a cell or in an artificial cell model using a cell-free translational system.

Means for Solving the Problems

The present invention has been achieved for attaining the object. Specifically, according to one embodiment, the present invention provides an mRNA comprising a small RNA-binding site located 5' to the ribosome-binding site and a nucleotide sequence located 5' to the small RNA-binding site, the nucleotide sequence being complementary to the ribosome-binding site. This mRNA is also referred to as an ON switch mRNA.

According to another embodiment, the present invention provides a method for translational regulation of mRNA, comprising mixing the mRNA with a small RNA complementarily binding to the small RNA-binding site in the mRNA.

According to a further embodiment, the present invention provides a translation/expression regulation system comprising the mRNA.

According to a further embodiment, the present invention provides an mRNA comprising a small RNA-binding site located 3' to the start codon and a nucleotide sequence located 3' to the small RNA-binding site, the nucleotide sequence encoding a protein. This mRNA is also referred to as an OFF switch mRNA.

According to a further embodiment, the present invention provides a method for translational regulation of mRNA, comprising mixing the mRNA with a small RNA complementarily binding to the small RNA-binding site, and a translation/expression regulation system comprising the mRNA.

According to a further embodiment, the present invention provides a translation/expression regulation system comprising the ON switch mRNA and the OFF switch mRNA, wherein the small RNA-binding sites in the ON switch mRNA and in the OFF switch mRNA have identical nucleotide sequences.

According to a further embodiment, the present invention provides an mRNA comprising: a small RNA-binding site located 5' to the ribosome-binding site; a nucleotide sequence located 5' to the small RNA-binding site, the nucleotide sequence being complementary to the ribosome-binding site; a nucleotide sequence located 5' to the nucleotide sequence complementary to the ribosome-binding site, the nucleotide sequence being identical to the small RNA-binding site; a sequence located 3' to the start codon, the sequence being identical to at least 6 consecutive bases of a small RNA; and a nucleotide sequence located 3' to the sequence identical to at least 6 consecutive bases of a small RNA, the nucleotide sequence encoding a protein. This mRNA is also referred to as a double ON switch mRNA.

According to a further embodiment, the present invention provides an artificial information conversion method comprising the steps of: detecting a small RNA expression level using the ON switch mRNA; and activating the translation of a target protein. According to a further embodiment, the present invention provides an artificial information conversion method comprising the steps of: detecting a small RNA expression level using the OFF switch mRNA; and repressing the translation of a target protein. These artificial information conversion methods further comprise the step of using a combination of the ON switch mRNA and the OFF switch mRNA specifically reacting with identical small RNAs, to simultaneously perform the activation of the translation of the protein encoded by the ON switch mRNA and the repression of the translation of the protein encoded by the OFF switch mRNA.

According to a further embodiment, the present invention provides a liposome comprising any of these mRNAs encapsulated therein.

According to a further embodiment, the present invention provides a liposome comprising an mRNA or DNA and a cell-free translational system encapsulated therein.

The liposome can be obtained by a production method comprising the steps of: mixing one or more phospholipids, the mRNA or DNA, the cell-free translational system, and an aqueous solution into an oily liquid to form a W/O emulsion in which the mRNA or DNA and the cell-free translational system are encapsulated in the phospholipid vesicle; adding an oily liquid containing outer membrane lipids dissolved therein, to an aqueous phase to form a molecular membrane in which the lipids are arranged at the oil/water interface; and adding the W/O emulsion to the oil phase side of the interface and moving the W/O emulsion to the aqueous phase side of the interface such that the outer membrane lipid is added outside of the W/O emulsion to form a liposome.

According to a further embodiment, the present invention provides a method for real-time monitoring of intraliposomal protein translation reaction, comprising the step of microscopically observing the liposome after the liposome formation step.

Advantage of the Invention

The present invention has the advantage that an mRNA according to the present invention can perform translational regulation of a desired gene in response to the presence of a small RNA.

BRIEF DESCRIPTION OF THE DRAWINGS

FIG. 3A is a schematic diagram showing miRNA164 (SEQ ID NO:29)

FIG. 13 is a microscopic photograph showing the fluorescence of a liposome comprising an EGFP-encoding DNA and a cell-free translational system encapsulated therein, upon activation (0 min) and subsequently at 15-minute intervals (i.e., 15 min, 30 min, 45 min, 60 min, and 135 min after the activation);

FIG. 14A is a microscopic photograph showing the fluorescence of a liposome upon activation of an RNA-responsive artificial RNA switch (0 min), FIG. 14B is a microscopic photograph showing the fluorescence of the liposome 60 min after the activation;

DESCRIPTION OF SYMBOLS

Figure 1:
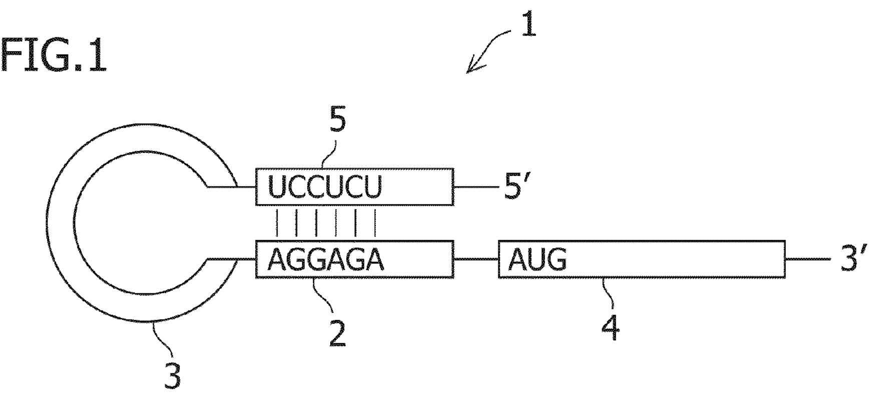
FIG. 1 is a diagram showing an mRNA according to the first embodiment in a switch OFF state.

1 mRNA
2 ribosome-binding site
3 small RNA-binding site
4 open reading frame
4*a* start codon AUG
4*b* nucleotide sequence encoding a gene of a protein to be expressed
5 nucleotide sequence complementary to the ribosome-binding site
6 small RNA
7 ribosome
8 sequence complementarily binding to a portion of the small RNA-binding site
10 PDMS chamber
11 egg PC
12 egg PC
13 Feeding Solution
14 emulsion
15 Liposome Inside Solution
16 liposome
20 ribosome-binding site
30 sequence complementary to a small RNA
40 nucleotide sequence encoding DsRed
41 open reading frame
41*a* start codon AUG
41*b* nucleotide sequence 41*b* encoding EGFP
50 sequence complementary to the ribosome-binding site
60 small RNA

BEST MODE FOR CARRYING OUT THE INVENTION

Hereinafter, the present invention will be described in detail with reference to the embodiments. However, the description below is not intended to limit the present invention.

An mRNA according to the first embodiment of the present invention is characterized by comprising a small RNA-binding site located 5' to the ribosome-binding site and a sequence located 5' to the small RNA-binding site, the sequence being complementary to the ribosome-binding site. An mRNA 1 shown in FIG. 1 comprises a ribosome-binding site 2, a small RNA-binding site 3, an open reading frame 4, and a sequence 5 complementary to the ribosome-binding site.

[mRNA]

The mRNA 1 according to this embodiment may be an arbitrary mRNA that has the ribosome-binding site 2 and has translational functions. The sequence of the open reading frame 4 is not limited to a particular sequence. Moreover, the mRNA 1 may be an mRNA having a 5'-terminal stem-loop structure (not shown) for enhancing its transcriptional efficiency. Examples of the 5'-terminal stem-loop structure include, but not limited to, usually known structures. Those skilled in the art can introduce an arbitrary stem-loop structure for enhancing transcriptional efficiency into the 5' end according to the standard method.

The sequence of the open reading frame 4 may have a gene that can be expressed into the desired protein, and has a start codon, though it is not limited to a particular sequence. For example, an mRNA having an open reading frame 4 having a gene encoding a fluorescent protein can be used for the purpose of confirming whether the translational functions act. Examples of the fluorescent protein include EGFP, GFP-UV, and DsRed. Their sequences are generally known.

In addition, the sequence of the open reading frame 4 may encode a protein that works as a particular pharmaceutical agent. Specifically, examples of the protein include, but not limited to, apoptosis-inducing proteins Bim and Bax, apoptosis-promoting BH3 peptides, and variants thereof

[Small RNA-Binding Site]

The small RNA-binding site 3 has a sequence complementary to a particular small RNA. The small RNA is a generic name for RNAs that have a base length of 10 bases to 80 bases and have the property of regulating cell functions through their interactions with RNAs or proteins. In this embodiment, a small RNA of any sequence and any base length can be used. Preferably, the small RNA itself does not form a stem structure at a temperature around 37° C.

One example of the small RNA includes an miRNA. The miRNA is an abbreviation of micro-RNA. The miRNA, which is a small, protein-noncoding RNA molecule, is thought to participate in various life phenomena such as development, differentiation, and proliferation. Approximately several hundreds of kinds of specific miRNA sequences have been identified in organisms such as *Arabidopsis*, humans, and mice, and these sequences are already known in databases such as miRbase.

More specifically, in this embodiment, *Arabidopsis*-derived miRNAs miR164, miR170, and miR171 can be used, though the miRNA is not limited thereto.

The small RNA-binding site 3 according to this embodiment can be set to a sequence complementary to a particular small RNA. Alternatively, the small RNA-binding site 3 may be complementary to not only the full nucleotide sequence of the small RNA but also at least 15 bases or more, preferably 20 bases or more, of the small RNA. Moreover, this complementary sequence may have 1 to 3 mutations in some cases. Examples of the cases particularly include the cases in which strong hydrogen bond can be formed when the site forming the complementary sequence is rich in GC.

The small RNA-binding site 3 is located 5' to the ribosome-binding site 2. In this embodiment, the term "5' to the ribosome-binding site 2" in the mRNA 1 refers to a position 1 to 15 bases (inclusive) distant from the ribosome-binding site 2, preferably a position 1 to 10 bases (inclusive) distant from the ribosome-binding site 2, more preferably 1 to 5 bases (inclusive) distant from the ribosome-binding site 2, toward the 5' end. This range can be determined within a range that can achieve the activation of translation reaction in response to a targeted substrate small RNA. In FIG. 1, a line is described between the small RNA-binding site 3 and the ribosome-binding site 2. However, the small RNA-binding site 3 and the ribosome-binding site 2 are not necessarily required to be adjacent to each other. In this embodiment, a nucleotide sequence that may be located between the small RNA-binding site 3 and the ribosome-binding site 2 is not limited to a particular nucleotide sequence.

[Sequence Complementary to Ribosome-Binding Site]

The sequence 5 complementary to the ribosome-binding site is located 5' to the small RNA-binding site 3 in the mRNA 1. The sequence 5 complementary to the ribosome-binding site is intended to complementarily bind to the ribosome-binding site 2 placed on the same mRNA 1 to form a stem structure. Thus, the sequence 5 complementary to the ribosome-binding site can specifically have UCUCCU from the 5' end. In this context, the ribosome-binding site is not limited to AGGAGA and is known to be an AG-rich sequence. Therefore, the sequence 5 is not limited thereto as long as the sequence is complementary to the ribosome-binding site. In this context, the sequence 5 complementary to the ribosome-binding site may further have a sequence complementary to approximately 1 to 10 bases located immediately 3' to the ribosome-binding site 2 and/or approximately 1 to 10 bases located immediately 5' thereto.

The sequence 5 complementary to the ribosome-binding site may be located immediately 5' to the small RNA-binding site 3 or may be placed via 1 to 10 bases, preferably 1 to 5 bases, downstream thereof. In FIG. 1, a line is described between the small RNA-binding site 3 and the sequence 5 complementary to the ribosome-binding site. However, the small RNA-binding site 3 and the sequence 5 complementary to the ribosome-binding site are not necessarily required to be adjacent to each other. In this embodiment, a nucleotide sequence that may be located between the small RNA-binding site 3 and the sequence 5 complementary to the ribosome-binding site is not limited to a particular nucleotide sequence.

[Action as RNA Switch]

The mRNA 1 having the characteristics as described above can act as an artificial RNA switch. Specifically, it can act to initiate translation in response to the presence of a particular small RNA. This action will be described with reference to the drawings. The mRNA 1 according to this embodiment assumes a structure shown in FIG. 1 (switch OFF state), in the absence of the particular small RNA, in a Hepes buffer at 25 to 42° C., preferably approximately 33 to 41° C. and pH of approximately 6.0 to 8.5, preferably approximately 6.5 to 8.0. Specifically, the ribosome-binding site 2 forms a complementary strand with the sequence 5 (located 5' to the ribosome-binding site) complementary to the ribosome-binding site to form a stem structure. Therefore, a ribosome, if any, cannot bind to the ribosome-binding site 2. Thus, the translation of the mRNA 1 does not occur. Further, in this state, the small RNA-binding site 3 forms a loop structure as shown in the diagram.

Figure 2:
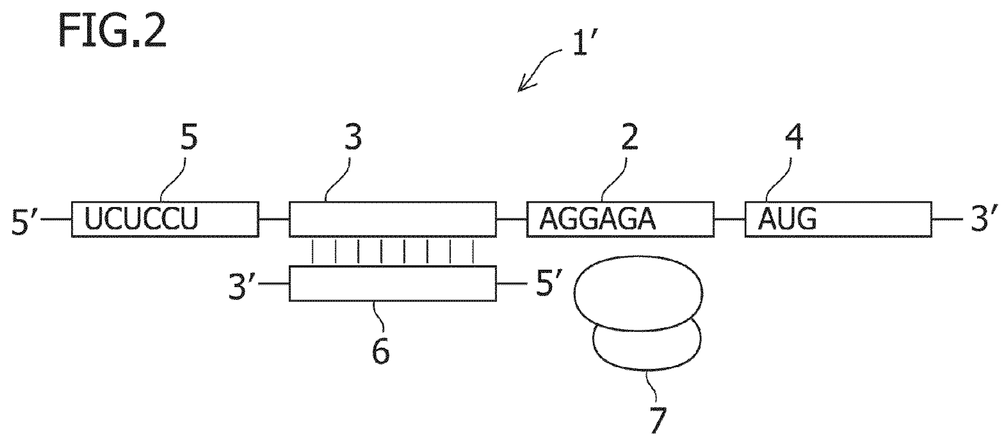
FIG. 2 is a diagram showing the mRNA according to the first embodiment in a switch ON state.

Next, a small RNA 6 is added in 0.25 to 20-fold amount (mol) with respect to the mRNA, to the mRNA assuming the structure shown in FIG. 1 in a Hepes buffer at 25 to 42° C., preferably around 33 to 41° C. and pH of approximately 6.0 to 8.5, preferably approximately 6.5 to 8.0. This small RNA 6 has a sequence complementary to the small RNA-binding site 3. The state in the presence of the miRNA 6 is shown in FIG. 2. In FIG. 2, the small RNA 6 complementarily binds to the small RNA-binding site 3. This binding deforms the stem structure of the ribosome-binding site 2, which is in turn placed in a state capable of binding to a ribosome 7. Thus, the ribosome 7, if any, initiates the translation of the mRNA 1 (switch ON) to form the particular protein.

Furthermore, translational regulation dependent on the amount of the small RNA added can be achieved by changing the amount of the small RNA added with respect to the amount of the mRNA. Moreover, translation can be switched OFF again by adding small RNA antisense thereto.

In light of the action, even a method for translational regulation of mRNA can be provided using the mRNA according to the first embodiment. This method comprises mixing the mRNA with a small RNA complementarily binding to the small RNA-binding site. Moreover, a method for translational regulation of mRNA can also be provided, which comprises mixing the mRNA with a small RNA complementarily binding to the small RNA-binding site. Furthermore, a translation/expression regulation system comprising the mRNA can also be provided. In this case, preferably, the system contains even a small RNA. Furthermore, an artificial information conversion method can also be provided, which comprises the steps of: detecting a small RNA expression level using the mRNA; and activating the translation of a target protein. In the artificial information conversion method, owing to the properties of the mRNA according to the first embodiment, the translation of the target protein is activated in response to the abundance, i.e., expression level, of the small RNA in a small RNA-expressing system to express the protein. In this way, information conversion can be achieved from the "input" of the small RNA to the "output" of the protein.

The mRNA according to the first embodiment can perform gene translation in response to the presence of a small RNA and its abundance. Moreover, an intracellular small RNA expression level is known to vary depending on biological reactions in vivo. The mRNA according to this embodiment has the advantage that such change in small RNA expression level can be detected using the mRNA.

Next, according to the second embodiment, the present invention provides a liposome comprising an mRNA or DNA and a cell-free translational system encapsulated therein. Moreover, the present invention provides a method for producing a liposome comprising an mRNA or DNA and a cell-free translational system encapsulated therein, comprising the steps of: mixing one or more phospholipids, the mRNA and/or DNA, the cell-free translational system containing proteins, and an aqueous solution into an oily liquid to form a W/O emulsion in which the cell-free translational system is encapsulated in the phospholipid vesicle; adding an oily liquid containing outer membrane lipids dissolved therein, to an aqueous phase to form a molecular membrane in which the lipids are arranged at the oil/water interface; and adding the W/O emulsion to the oil phase side of the interface and spontaneously moving the W/O emulsion to the aqueous phase side of the interface such that the outer membrane lipid is added outside of the W/O emulsion to form a liposome.

The mRNA or DNA encapsulated in the liposome may be an mRNA having an arbitrary open reading frame or a DNA encoding the mRNA sequence. Thus, the mRNA according to the first embodiment may also be used. Any of those expressed into an arbitrary protein in the liposome can be used. Moreover, when the expressions of two or more proteins are desired, two or more different DNAs or a combination of mRNA(s) and DNA(s) may be used.

The cell-free translational system encapsulated in the liposome is a composition that can cause extracellular expression of the mRNA or DNA. This system comprises ribosomes, several types of protein factors, amino acids, and buffers, etc. One example thereof can include, but not limited to, enzymes, *E. coli* ribosomes, aminoacyl tRNA synthetases (20 kinds), T7 RNA polymerase, and buffers (50 mM Hepes-KOH, pH 7.6, 100 mM K-Glu, 2 mM spermidine, 13 mM $Mg(OAc)_2$, 1 mM DTT, 0.3 mM each 20 amino acids, 560 D/ml tRNA mix, 10 mg/ml 10-formyl-5,6,7,8-tetrahydrofolic acid, 2 mM ATP, 2 mM GTP, 1 mM UTP, 1 mM CTP, 20 mM CP in terms of final concentrations). Specific components contained in the cell-free translational system are described in detail in Shimizu et al., Methods 36 (2005) 299-304. Those skilled in the art can construct the cell-free translational system based on the document. Particularly, a cell-free translational system comprising purified proteins is preferable. The cell-free translational system comprising purified proteins is preferably used in the liposome capable of constituting an artificial cell system according to this embodiment, because it is less likely to cause RNA decomposition owing to little RNase and has definite components.

The liposome comprising mRNA encapsulated therein can be produced based on the descriptions of PCT/JP2006/317517 and Langmuir 2006, 22, 9824-9828, which are incorporated herein by reference in their entirety.

Specifically, egg PC (egg-derived phosphatidyl choline) or a lipid selected from phosphatidyl serine and its derivatives and phosphatidyl ethanolamine and its derivatives, the mRNA or DNA encoding the mRNA sequence, an miRNA, the cell-free translational system containing proteins, and an aqueous solution are mixed into an oily liquid to form a W/O emulsion. Next, an oily liquid containing outer membrane lipids (egg PC or selected from phosphatidyl serine and its derivatives and phosphatidyl ethanolamine and its derivatives) dissolved therein is added to an aqueous phase to form a molecular membrane in which the outer membrane lipids are arranged at the oil/water interface.

In this context, the inner membrane phospholipid is preferably formulated to have a concentration of 0.5 mM to 0.75 mM in the oily liquid. When two or more inner membrane phospholipids are used, the total concentration thereof is preferably set to this range. Moreover, the ratio between the oily liquid and the aqueous solution formulated is preferably set to aqueous solution/oily liquid=1/1000 to 1/10 by volume.

The oily liquid is not particularly limited as long as it stably disperses therein the inner membrane phospholipid. For example, mineral oil can be used. Examples of the aqueous solution can include, but not particularly limited to, liquids having properties necessary for containing the mRNA and causing the desired reaction.

Osmotic pressure conditions for maintaining an appropriate state in the liposome, specifically, without causing contraction or rupture preferably involve keeping the external pressure of the liposome smaller than the internal pressure thereof.

In this way, translational regulation or artificial information conversion can be performed intraliposomally by encapsulating the mRNA or DNA encoding the mRNA sequence, the miRNA, and the cell-free translational system containing proteins into the liposome. This enables construction of an artificial cell system. Moreover, likewise, translation reaction can be constructed intraliposomally by encapsulating the mRNA or DNA encoding the mRNA sequence and the cell-free translational system containing proteins into the liposome.

The thus-obtained liposome comprising the cell-free translational system tends to accumulate at the oil/water interface when formed through the steps. Therefore, many focused liposomes can be detected simultaneously under a microscope. Using this property, a modification of this embodiment provides a method for real-time monitoring of intraliposomal protein translation reaction, comprising the step of microscopically observing the liposome after the liposome formation step. This monitoring method has the advantage that it can allow real-time monitoring of intraliposomal switch ON/OFF of translation.

In this way, the second embodiment of the present invention has the advantage that a translation reaction system can be encapsulated in all liposomes. Moreover, since the liposomes remain at the oil/water interface, focused images of a plurality of liposomes can be obtained under a microscope. This also enables real-time monitoring of translation reaction within the plurality of liposomes.

Methods for constructing a translational regulatory system using an artificial RNA switch and introducing the artificial RNA switch into liposomes will be shown. This approach is a technique of constructing an artificial RNA switch system that causes structural change in response to a particular RNA to regulate gene translation reaction, and of introducing this artificial RNA switch to liposomes and regulating translation reaction in the liposomes. Hereinafter, a specific experimental example will be shown. The construction of the artificial RNA switch system is summarized as follows: an input substrate (small RNA, etc.) binds to the upstream "substrate RNA-recognizing RNA motif" inserted in the mRNA, and the binding between the substrate and the RNA motif induces the structural change of the mRNA translation initiation region such that the translation of a target protein (GFP, etc.) can be regulated depending on the binding of a ribosome to the mRNA.

Next, according to the third embodiment, the present invention provides an mRNA having a small RNA-binding site located 3' to the start codon. The mRNA according to this embodiment can function as an OFF switch mRNA that regulates translation in an ON-to-OFF manner in response to a small RNA.

Figure 15:
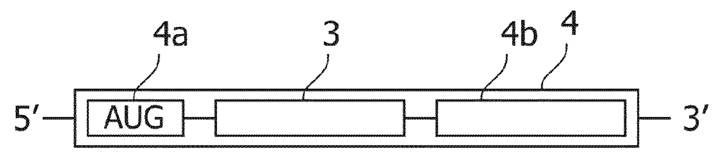
FIG. 15 is a diagram showing an mRNA according to the third embodiment in a switch ON state.

FIG. 15 shows a schematic diagram of the mRNA according to this embodiment. The mRNA shown in FIG. 15 has a small RNA-binding site 3 located immediately 3' to a start codon AUG (4*a*). A nucleotide sequence 4*b* encoding a gene of a protein to be expressed is located immediately 3' to the small RNA-binding site 3. Specifically, in this mRNA, its open reading frame comprises the start codon AUG (4*a*), the small RNA-binding site 3, and the nucleotide sequence 4*b* encoding a gene of a protein to be expressed, in this order from the 5' side.

In this embodiment, the small RNA may be the arbitrary small RNA described in the first embodiment. In the description below, an miRNA is used as the small RNA. The small RNA-binding site 3 is a sequence complementary to an miRNA. This complementary sequence may have 1 to 3 mutations in some cases as long as it complementarily binds to the target miRNA. Examples of the cases particularly include the cases in which strong hydrogen bond can be formed when the site forming the complementary sequence is rich in GC. In this embodiment, the mRNA shown in the diagram has the small RNA-binding site 3 immediately 3' to the start codon AUG (4*a*) without additional bases intervening therebetween. However, additional bases may be located between the start codon AUG (4*a*) and the small RNA-binding site 3. Specifically, relatively short bases such as approximately 3, 6, or 9 bases, whose base number is a multiple of 3 can also be present therebetween. The base number is set to a multiple of 3 for preventing the frameshift of translation.

The nucleotide sequence 4*b* encoding a gene of a protein to be expressed may be a nucleotide sequence encoding a gene of an arbitrary protein. Examples of the protein include, but not limited to, fluorescent proteins serving as a marker, specifically, DsRed and EGFP. The mRNA shown in the diagram has the nucleotide sequence 4*b* encoding a gene of a protein, immediately 3' to the small RNA-binding site 3 without additional bases intervening therebetween. However, when the base number of the small RNA-binding site 3 is not a multiple of 3, one or two bases are inserted between the small RNA-binding site 3 and the nucleotide sequence 4*b* encoding a gene of a protein. This is because frameshift for the protein is prevented. Moreover, even when the base number of the small RNA-binding site 3 is a multiple of 3, additional bases may be present between the small RNA-binding site 3 and the nucleotide sequence 4*b* encoding a gene of a protein. Specifically, relatively short bases such as approximately 3, 6, or 9 bases, whose base number is a multiple of 3 can also be present therebetween.

In the mRNA shown in FIG. 15, a ribosome-binding site 5' to the start codon AUG is not shown. However, the ribosome-binding site may be present or may be absent for mRNAs derived from eukaryotic cells.

The mRNA thus constituted according to the third embodiment of the present invention functions as an OFF switch mRNA in the presence of a particular small RNA. The functions of such an mRNA will be described below.

Figure 16:
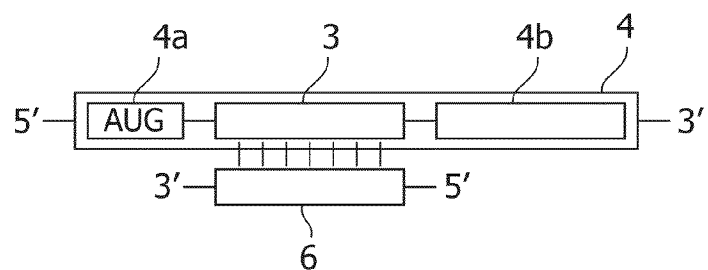
FIG. 16 is a diagram showing the mRNA according to the third embodiment in a switch OFF state.

In the absence of the particular small RNA, i.e., an miRNA 6 specifically binding to the mRNA according to the third embodiment, the mRNA is translated under conditions involving 25 to 42° C. and pH 6 to 8.5 to form the desired protein having, at the N terminus, an amino acid encoded by the miRNA. By the addition of the miRNA 6 thereto, the miRNA 6 forms a complementary double strand through its specific binding with the mRNA designed to have a sequence specifically binding thereto (small RNA-binding site 3). A schematic diagram of the molecule in this state is shown in FIG. 16. As a result, ribosome-catalyzed mRNA translation is inhibited to repress protein expression.

In this way, the use of the mRNA according to this embodiment and the small RNA specifically binding thereto enables ON-to-OFF regulation of protein translation. Accordingly, examples of modifications of the third embodiment include a translation/expression regulation system comprising the mRNA thus constituted and a small RNA specifically binding thereto, and a method for translational regulation of mRNA, comprising mixing the mRNA with a small RNA complementarily binding to the small RNA-binding site.

The applicative aspect of this embodiment can achieve translational regulation within PURE system and is useful as a tool for artificial signal cells.

Furthermore, in an artificial information conversion method, owing to the properties of the mRNA according to the third embodiment, the translation of the target protein is repressed in response to the abundance, i.e., expression level, of the small RNA in a small RNA-expressing system to inhibit protein expression. In this way, information conversion can be achieved from the "input" of the small RNA to the "output" of the protein.

Next, the fourth embodiment of the present invention will be described. The fourth embodiment of the present invention relates to an artificial translational system. Specifically, it relates to an artificial translational system comprising the ON switch mRNA described in the first embodiment, the OFF switch mRNA described in the third embodiment, a small RNA specifically binding to both the mRNAs.

Figure 17A:
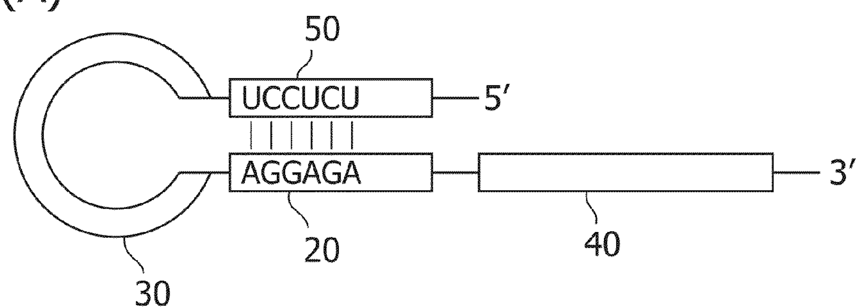
FIG. 17A shows an ON switch mRNA according to the fourth embodiment in a switch OFF state.
Figure 17B:
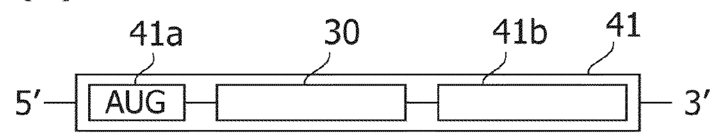
FIG. 17B shows an OFF switch mRNA according to the fourth embodiment in a switch ON state.
Figure 17C:
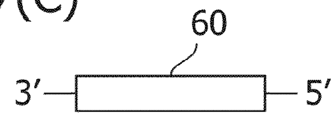
FIG. 17C shows a small RNA specifically binding to both the mRNAs of FIGS. 17A and 17B.

FIG. 17(A) shows a schematic diagram of the ON switch mRNA constituting the artificial translational system according to this embodiment; FIG. 17(B) shows a schematic diagram of the OFF switch mRNA constituting it; and FIG. 17(C) shows a schematic diagram of the small RNA constituting it. In this embodiment, the case will be illustrated in which a protein expressed by the ON switch mRNA is DsRed and a protein expressed by the OFF switch mRNA is EGFP. However, this combination of the expressed proteins is shown for illustrative purposes and is not intended to limit the present invention.

The ON switch mRNA of this embodiment, as shown in the diagram, comprises a DsRed-encoding nucleotide sequence 40 located immediately 3' to a ribosome-binding site 20 and a sequence 30 located 5' to the ribosome-binding site, the sequence 30 being complementary to a small RNA. The ON switch mRNA further comprises, 5' thereto, a sequence 50 complementary to the ribosome-binding site. This ON switch mRNA forms a stem-loop structure, as shown in FIG. 17(A), in the absence of a small RNA 60. In this case, the ribosome-binding site 20 is blocked. Therefore, the ON switch mRNA in this state is not translated even under translatable conditions, resulting in no DsRed production.

On the other hand, the OFF switch mRNA of this embodiment, as shown in FIG. 17(B), comprises a sequence 30 located immediately 3' to a start codon AUG (41*a*), the sequence 30 being complementary to a small RNA 60. The OFF switch mRNA further comprises an EGFP-encoding nucleotide sequence 41*b* located 3' to the sequence 30 complementary to a small RNA 60. Moreover, a ribosome-binding site may be present (not shown) 5' to the start codon AUG (41*a*) or may be absent. Such an OFF switch mRNA is translated under translatable conditions in the absence of the small RNA 60 to produce the protein EGFP.

The small RNA 60 shown in FIG. 17(C) is a sequence capable of forming a complementary strand through its specific binding to the sequence 30 complementary to the small RNA 60, both in the ON switch mRNA and in the OFF switch mRNA.

Figure 18A:
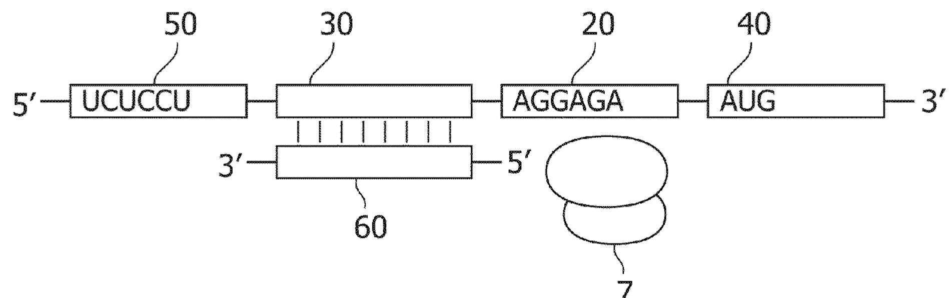
FIG. 18A shows the state where the small RNA of FIG. 17C is added to the ON switch mRNA of FIG. 17A.
Figure 18B:
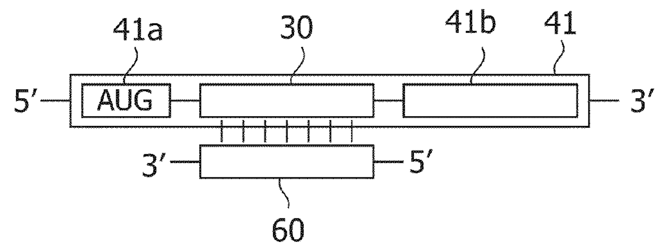
FIG. 18B shows the state where the small RNA of FIG. 17C is added to the OFF switch mRNA of FIG. 17B.

Next, FIG. 18 schematically showing the state of each molecule in the coexistence of the ON switch mRNA, the OFF switch mRNA, and the small RNA 60. In the ON switch mRNA shown in FIG. 18(A), the small RNA 60 forms a complementary strand through its specific binding to the sequence 30 having a loop structure in FIG. 17(A). As a result, the stem-loop structure is deformed, and the ribosome-binding site 20 is in turn placed in a state capable of binding to a ribosome. On the other hand, in the OFF switch mRNA shown in FIG. 18(B), the small RNA 60 forms a complementary strand through its specific binding to the sequence 30 located immediately downstream of the start codon. As a result, the OFF switch mRNA shown in FIG. 18(B) cannot be translated in this state.

In such a state, which is a translatable state, shown in FIG. 18(A), a ribosome can bind to the ON switch mRNA. Accordingly, the gene in the open reading frame 40 is expressed in the presence of the ribosome and under appropriate other conditions to produce DsRed. On the other hand, in the OFF switch mRNA, a double strand is formed immediately downstream of the start codon. Therefore, the mRNA cannot be translated. As a result, EGFP encoded by the sequence 41*b* is not produced.

In this way, according to the fourth embodiment, two mRNAs differing in behavior in response to the presence of the same small RNA can be used as switches.

The applicative aspect of this embodiment can achieve translational regulation within PURE system and is useful as a tool for artificial signal cells.

Furthermore, in an artificial information conversion method, owing to the properties of the ON switch mRNA and the OFF switch mRNA according to the fourth embodiment, the translation of the target protein encoded by the ON switch mRNA is activated in response to the abundance, i.e., expression level, of the small RNA in a small RNA-expressing system to express the protein. At the same time, the translation of another target protein encoded by the OFF switch mRNA is repressed in response to the abundance, i.e., expression level, of the small RNA to inhibit protein expression. In this way, information conversion can be achieved from the "input" of the small RNA to the separate "outputs" of two different proteins.

Next, the fifth embodiment of the present invention will be described. The fifth embodiment provides an mRNA that functions as an ON switch in response to the addition of a small RNA. The mRNA according to this embodiment is referred to as a double ON switch mRNA.

Figure 19:
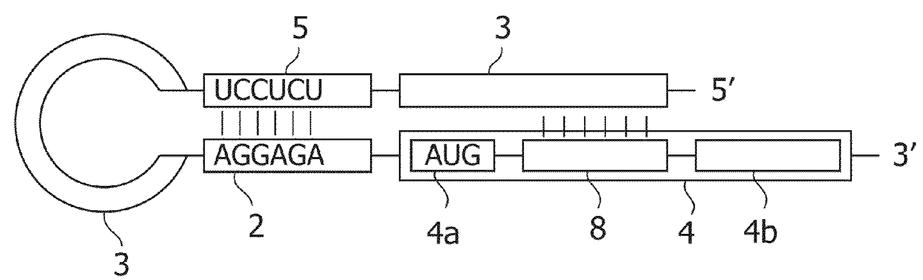
FIG. 19 shows a double ON switch mRNA according to the fifth embodiment in a switch OFF state.

FIG. 19 schematically shows the secondary structure of the mRNA according to this embodiment. The mRNA according to this embodiment comprises a small RNA-binding site 3, a sequence 5 complementary to the ribosome-binding site, another small RNA-binding site 3, a ribosome-binding site 2, and an open reading frame 4, in this order from the 5' side. The open reading frame 4 comprises a start codon AUG 4*a*, a sequence 8 complementarily binding to a portion of the small RNA-binding site 3, and a nucleotide sequence 4*b* encoding a gene of a protein to be expressed, in this order from the 5' side.

In this context, each small RNA-binding site 3 can have a nucleotide sequence that forms a reverse complement of a particular small RNA. This complementary sequence may have 1 to 3 mutations in some cases as long as it complementarily bind to the target small RNA. Moreover, these two small RNA-binding sites 3 preferably have identical sequences.

The sequence 8 complementarily binding to a portion of the small RNA-binding site 3 has a sequence identical to at least 6 consecutive bases of the particular small RNA. The number of the consecutive bases is preferably 6 bases or more and is a multiple of 3 equal to or smaller than the base number of the small RNA. Specifically, the number of the consecutive bases is preferably set to approximately 6 bases, 9 bases, 12 bases, 15 bases, or 18 bases, though the base number is not limited thereto. The reason for such a constitution is that a complementary strand is formed with the small RNA while frameshift of the protein to be expressed is prevented. The sequence 8 complementarily binding to a portion of the small RNA-binding site 3 may comprise a sequence identical to the particular small RNA and an additional sequence. In such a case as well, the base number of the sequence 8 is a multiple of 3.

The mRNA shown in FIG. 19 forms a stem-loop structure, as shown in the diagram, in the absence of the particular small RNA. In this case, the stem moiety contains a first complementary strand moiety formed by the sequence 5 complementary to the ribosome-binding site and the ribosome-binding site 2 and a second complementary strand moiety formed by the small RNA-binding site 3 and the sequence 8 complementarily binding to a portion of the small RNA-binding site 3. The ribosome-binding site 2 is blocked by the formed complementary strand. Therefore, a ribosome, if any, cannot bind to the ribosome-binding site 2. Accordingly, the double ON switch mRNA in this state is not translated even under translatable conditions, resulting in no production of the protein encoded by the sequence 4*b*.

In the mRNA according to the fifth embodiment, the advantage of the presence of the first and second complementary strand moieties is that owing to the action of these two complementary strands, a stable OFF state can be formed in the absence of the particular small RNA and an ON state can be formed efficiently in the presence of the small RNA.

Figure 20:
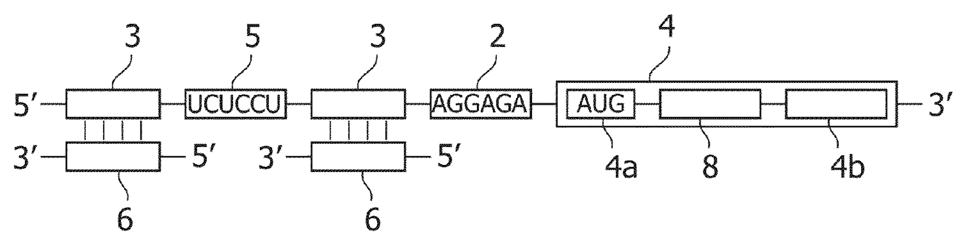
FIG. 20 shows the double ON switch mRNA according to the fifth embodiment in a switch ON state.

Next, FIG. 20 schematically shows the secondary structure of the mRNA coexisting with particular small RNAs 6. In this case, the particular small RNAs 6 specifically bind to both the two small RNA-binding sites 3 on the mRNA to form complementary strands. As a result, the stem-loop structure is deformed such that the ribosome-binding site 2 is unblocked. Accordingly, translation proceeds in the presence of the ribosome and under appropriate other conditions to produce the protein encoded by the nucleotide sequence 4*b*.

In this way, the fifth embodiment has the advantage that depending on the sequences of the small RNA-binding sites, the first and second complementary strand moieties can act cooperatively to prepare an efficient OFF-to-ON switch, when the mRNA structure cannot form stable OFF and ON states.

Example 1

[Preparation of Original EGFP and RNA-Responsive Artificial RNA Switches]

Original EGFP and RNA-responsive artificial RNAs (EGFP) were prepared (EGFP, SEQ ID NO: 1) by performing twice or three times PCR using pEGFP (manufactured by Clontech). All primers described here were synthesized by Hokkaido System Science Co., Ltd.

[Preparation of Original EGFPmRNA]

pEGFP was used as a template to perform 1st PCR using EGFP fwd (SEQ ID NO: 2) and EGFP rev (SEQ ID NO: 3) as primers. 50 μL of reaction solution contained a mixture of 25 ng of pEGFP, 1.5 μL of 10 μM each DNA primers, 5 μL of 2 mM dNTPs, 5 μL of 10×KOD-PLUS-buffer ver. 2, 2 μL of 25 mM $MgSO_4$, and 1 μL of KOD-PLUS-DNA polymerase. Reaction was performed by initially performing incubation at 94° C. for 2 minutes and then 20 cycles each involving 94° C. for 15 seconds, 50° C. for 30 seconds, and 68° C. for 1 minute.

In the description below, only a template and primers will be shown because PCR was performed under the same conditions as above.

After the reaction, the reaction solution was subjected to phenol treatment and ethanol precipitation and dissolved in a nondenaturing dye (30% glycerin, 0.075% xylene cyanol, 0.075% bromophenol blue, 69.85% ultrapure water). The band of interest was separated and excised using low melting point agarose SEAPLAQUE GTG AGAROSE (FMC Corp.). The excised agarose fragment was supplemented with 200 μL of TE, then incubated at 65° C. for 30 min, and then subjected to 3 phenol treatments, diethyl ether treatment, and ethanol precipitation for DNA purification (EGFP 1st PCR, SEQ ID NO: 4). Next, EGFP 1st PCR was used as a template to perform 2nd PCR in the same way as above using Universal primer (SEQ ID NO: 5) and EGFP Rev as primers. After the reaction, separation and purification were performed in the same way as above, and the purification product was dissolved in ultrapure water, followed by concentration measurement using DU640 SPECTROPHOTOMETER (manufactured by Beckman Coulter, Inc.). This product is referred to as Original EGFP template (SEQ ID NO: 6). Original EGFP template was used as a template to perform transcription reaction using MEGAshortscript (trademark) (manufactured by Ambion, Inc.). The transcription reaction using MEGAshortscript was performed as follows. 1 μg of template DNA dissolved in ultrapure water, 2 μL of T7 10× Reaction Buffer, 2 μL of T7 ATP Solution (75 mM) (the same recipe for CTP, GTP, and UTP), and 2 μL of T7 Enzyme Mix were mixed and adjusted with ultrapure water to the whole amount of 20 μL. This reaction solution was reacted at 37° C. for 4 hours to overnight. After the reaction, the solution was supplemented with 1 μL of TURBO DNase and incubated at 37° C. for 15 minutes to decompose the template DNA. Original EGFP mRNA (SEQ ID NO: 7) obtained through the transcription reaction was purified using RNeasy MinElute (trademark) Cleanup Kit (QIAGEN GmbH). The purification using RNeasy MinElute (trademark) Cleanup Kit was performed as follows.

The transcription reaction solution was adjusted to 100 μL by the addition of 80 μL of ultrapure water, further supplemented with 350 μL of Buffer RLT, and sufficiently mixed. 250 μL of ethanol was added thereto and completely mixed by pipetting. The sample was applied to RNeasy MinElute Spin Column loaded in a 2-mL collection tube and centrifuged at 10,000 rpm for 15 seconds using a high-speed refrigerated microcentrifuge MX-100 (manufactured by TOMY SEIKO CO., LTD.), and the flow-through fraction was discarded. The spin column was transferred to a new 2-ml collection tube, and 500 μL of Buffer RPE was added onto the spin column using a pipette. The sample was centrifuged at 10,000 rpm for 15 seconds, and the flow-through fraction was discarded. After addition of 500 μL of 80% ethanol to the RNeasy MinElute Spin Column, the sample was centrifuged at 10,000 rpm for 2 minutes, and the flow-through fraction was discarded. The RNeasy MinElute Spin Column was transferred to a new 2-ml collection tube. The sample was centrifuged at 14,000 rpm for 5 minutes with the spin column cap opened, and the flow-through fraction was discarded. The spin column was transferred to a new 1.5-ml collection tube, and 20 μL of ultrapure water was added to the center of the silica gel membrane. The sample was centrifuged at 14,000 rpm for 5 minutes for elution. This eluate was used in concentration measurement using DU640 SPECTROPHOTOMETER.

[Preparation of RNA-Responsive Artificial RNA (5' miR164-Responsive EGFP)]

Figure 3B:
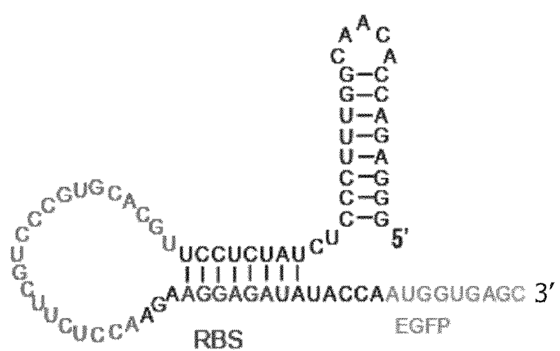
FIG. 3B is a schematic diagram showing the secondary structure of 5' miR164-responsive EGFP mRNA (SEQ ID NO:49)

EGFP 1st PCR was used as a template to perform 2nd PCR in the same way as above using 5' UTR-miRNA164 fwd (SEQ ID NO: 8) and EGFP rev as primers. After the reaction, separation and purification were performed in the same way as above. This product is referred to as 5' miR164-responsive EGFP 2nd PCR (SEQ ID NO: 9). Next, 5' miR164-responsive EGFP 2nd PCR was used as a template to perform 3rd PCR in the same way as above using T7-stem-loop uni (SEQ ID NO: 10) and EGFP rev as primers. After the reaction, separation and purification were performed in the same way as above, and the purification product was dissolved in ultrapure water, followed by concentration measurement using DU640 SPECTROPHOTOMETER. This product is referred to as 5' miR164-responsive EGFP template (SEQ ID NO: 11). 5' miR164-responsive EGFP template was used as a template to perform transcription reaction in the same way as above using MEGAshortscript (trademark). 5' miR164-responsive EGFP mRNA (SEQ ID NO: 12) obtained through the transcription reaction was purified in the same way as above using RNeasy MinElute (trademark) Cleanup Kit, followed by concentration measurement. FIG. 3B is a schematic diagram showing the secondary structure of the 5' miR164-responsive EGFP mRNA. FIG. 3A is a diagram showing miRNA164.

[Preparation of RNA-Responsive Artificial RNA (5' miR164-Responsive DsRed-Monomer)]

An RNA-responsive artificial RNA (DsRed-Monomer) was prepared by performing three times PCR using pDsRed-Monomer (manufactured by Clontech) (DsRed-Monomer, SEQ ID NO: 13). pDsRed-Monomer was used as a template to perform 1st PCR in the same way as above using DsRed-Monomer fwd (SEQ ID NO: 14) and DsRed-Monomer rev (SEQ ID NO: 15) as primers. After the reaction, separation and purification were performed in the same way as above. This product is referred to as DsRed-Monomer 1st PCR (SEQ ID NO: 16). Next, DsRed-Monomer 1st PCR was used as a template to perform 2nd PCR in the same way as above using 5' UTR-miRNA164 fwd and DsRed-Monomer rev as primers. After the reaction, separation and purification were performed in the same way as above. This product is referred to as 5' miR164-responsive DsRed-Monomer 2nd PCR (SEQ ID NO: 17). Further, 5' miR164-responsive DsRed-Monomer 2nd PCR was used as a template to perform 3rd PCR in the same way as above using T7-stem-loop uni and DsRed-Monomer rev as primers. After the reaction, separation and purification were performed in the same way as above, and the purification product was dissolved in ultrapure water, followed by concentration measurement using DU640 SPECTROPHOTOMETER. This product is referred to as 5' miR164-responsive DsRed-Monomer template (SEQ ID NO: 18). 5' miR164-responsive DsRed-Monomer template was used as a template to perform transcription reaction in the same way as above using MEGAshortscript (trademark). 5' miR164-responsive DsRed-Monomer mRNA (SEQ ID NO: 19) obtained through the transcription reaction was purified in the same way as above using RNeasy MinElute (trademark) Cleanup Kit, followed by concentration measurement.

[Preparation of RNA-Responsive Artificial RNA (5' miR170-Responsive EGFP)]

EGFP 1st PCR was used as a template to perform 2nd PCR in the same way as above using 5' UTR-miRNA170 fwd (SEQ ID NO: 20) and EGFP rev as primers. After the reaction, separation and purification were performed in the same way as above. This product is referred to as 5' miR170-responsive EGFP 2nd PCR (SEQ ID NO: 21). Next, 5' miR170-responsive EGFP 2nd PCR was used as a template to perform 3rd PCR in the same way as above using T7-stem-loop uni and EGFP rev as primers. After the reaction, separation and purification were performed in the same way as above, and the purification product was dissolved in ultrapure water, followed by concentration measurement using DU640 SPECTROPHOTOMETER. This product is referred to as 5' miR170-responsive EGFP template (SEQ ID NO: 22). 5' miR170-responsive EGFP template was used as a template to perform transcription reaction in the same way as above using MEGAshortscript (trademark). 5' miR170-responsive EGFP mRNA (SEQ ID NO: 23) obtained through the transcription reaction was purified in the same way as above using RNeasy MinElute (trademark) Cleanup Kit, followed by concentration measurement.

[Preparation of RNA-Responsive Artificial RNA (5' miR171-Responsive EGFP)]

EGFP 1st PCR was used as a template to perform 2nd PCR in the same way as above using 5' UTR-miRNA171 fwd (SEQ ID NO: 24) and EGFP rev as primers. After the reaction, separation and purification were performed in the same way as above. This product is referred to as 5' miR171-responsive EGFP 2nd PCR (SEQ ID NO: 25). Next, 5' miR171-responsive EGFP 2nd PCR was used as a template to perform 3rd PCR in the same way as above using T7-stem-loop uni and EGFP rev as primers. After the reaction, separation and purification were performed in the same way as above, and the purification product was dissolved in ultrapure water, followed by concentration measurement using DU640 SPECTROPHOTOMETER. This product is referred to as 5' miR171-responsive EGFP template (SEQ ID NO: 26). 5' miR171-responsive EGFP template was used as a template to perform transcription reaction in the same way as above using MEGAshortscript (trademark). 5' miR171-responsive EGFP mRNA (SEQ ID NO: 27) obtained through the transcription reaction was purified in the same way as above using RNeasy MinElute (trademark) Cleanup Kit, followed by concentration measurement.

Example 2

[Translational Regulation Assay Using Cell-Free Expression System of RNA-Responsive Artificial RNA Switch]

A cell-free expression system PURE system was used for confirming the translational regulation of an RNA-responsive artificial RNA switch. The PURE system is composed of Solution A and Solution B. In the description below, these solutions are simply referred to as Solutions A and B, respectively. Solution A has the composition involving 100 mM Hepes-KOH (pH 7.6), 200 mM L-Glutamic acid Monopotassium salt, 4 mM spermidine, 26 mM $Mg(OAc)_2$, 2 mM DTT, 1120 D/ml tRNA mix, 20 μg/ml 10-formyl-5,6,7,8-tetrahydrofolic acid, 4 mM ATP, 4 mM GTP, 2 mM CTP, 2 mM UTP, 40 mM creatine phosphate, and 0.6 mM each 20 amino acids. Solution B is composed mainly of T7 RNA polymerase, IF1, IF2, IF3, EF-G, EF-Tu, EF-Ts, RF1, RF2, RF3, RRF, etc., which are proteins necessary for transcription and translation. Hereinafter, assay on each RNA-responsive artificial RNA switch and its results will be shown.

[Assay on 5' miR164-Responsive EGFP]

Figure 4:
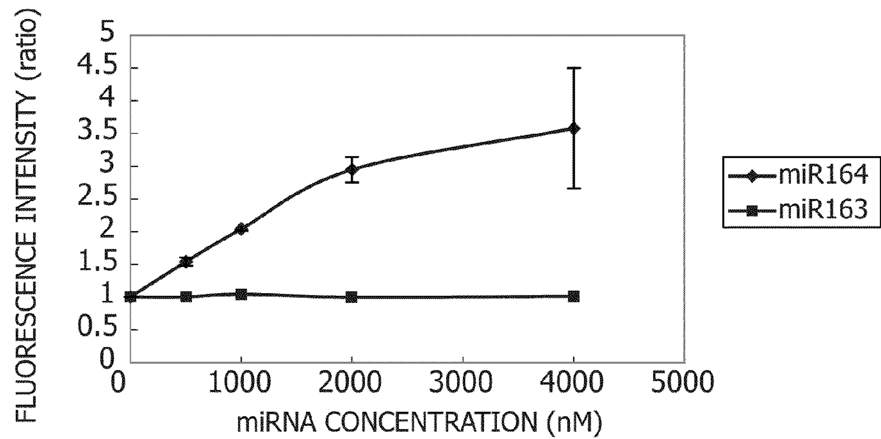
FIG. 4 is a graph showing assay on 5' miR164-responsive EGFP.

Five solutions each containing a mixture of 1 μL of 20 μM 5' miR164-responsive EGFP, 1 μL of ultrapure water, 5 μL of Solution A, and 2 μL of Solution B were prepared and supplemented with 1 μL each of 40 μM, 20 μM, 10 μM, 5 μM, and 0 μM synthesized miRNA164 (Hokkaido System Science Co., Ltd., SEQ ID NO: 29), respectively, to adjust the whole amount of 10 μL. The solutions were reacted at 37° C. for 75 minutes. After the reaction, each solution was adjusted with ultrapure water to 200 μL and measured at an excitation wavelength of 485 nm and an absorption wavelength of 535 nm using infinite F200 (manufactured by TECAN Trading AG) (FIG. 4).

For negative controls, five solutions each containing a mixture of 1 μL of 20 μM 5' miR164-responsive EGFP, 1 μL of ultrapure water, 5 μL of Solution A, and 2 μL of Solution B were prepared and supplemented with 1 μL each of 40 μM, 20 μM, 10 μM, 5 μM, and 0 μM synthesized miRNA163 (Hokkaido System Science Co., Ltd., SEQ ID NO: 28), respectively, to adjust the whole amount of 10 μL. The solutions were reacted at 37° C. for 75 minutes. After the reaction, each solution was adjusted with ultrapure water to 200 μL and measured at an excitation wavelength of 485 nm and an absorption wavelength of 535 nm using infinite F200 (TECAN Trading AG) (FIG. 4). This assay demonstrated that this RNA-responsive artificial RNA switch (5' miR164-responsive EGFP) specifically reacts with miRNA164 to perform translational regulation.

[Assay on 5' miR164-Responsive DsRed-Monomer]

Figure 5:
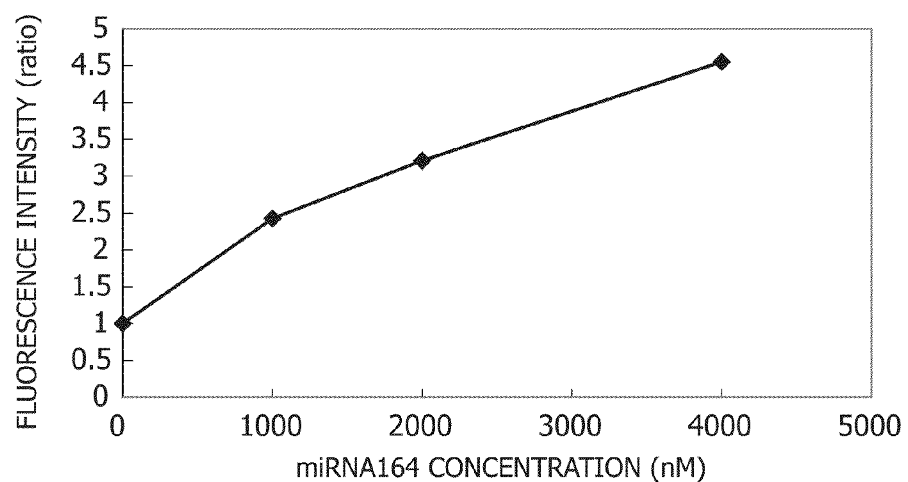
FIG. 5 is a graph showing assay on 5' miR164-responsive DsRed Monomer.

Four solutions each containing a mixture of 1 μL of 10 μM 5' miR164-responsive DsRed-Monomer, 1 μL of ultrapure water, 5 μL of Solution A, and 2 μL of Solution B were prepared and supplemented with 1 μL each of 40 μM, 20 μM, 10 μM, and 0 μM miRNA164, respectively, to adjust the whole amount of 10 μL. The solutions were reacted at 37° C. for 75 minutes. After the reaction, each solution was adjusted with ultrapure water to 200 μL and measured at an excitation wavelength of 535 nm and an absorption wavelength of 595 nm using infinite F200 (manufactured by TECAN Trading AG) (FIG. 5). This assay demonstrated that these RNA-responsive artificial RNA switches (5' miR164-responsive EGFP and 5' miR164-responsive DsRed-Monomer) are independent of the sequence of the open reading frame.

[Assay on 5' miR171-Responsive EGFP]

Figure 6:
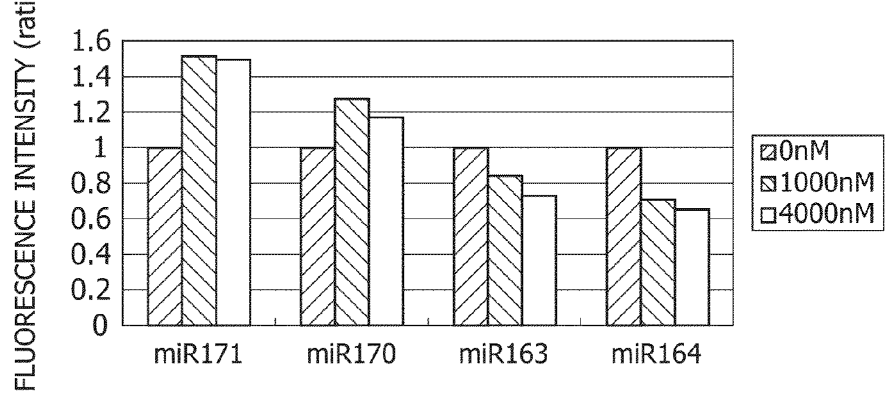
FIG. 6 is a graph showing assay on 5' miR171-responsive EGFP.

Three solutions each containing a mixture of 1 μL of 2 μM 5' miR171-responsive EGFP, 1 μL of ultrapure water, 5 μL of Solution A, and 2 μL of Solution B were prepared and supplemented with 1 μL each of 40 μM, 10 μM, and 0 μM synthesized miRNA171 (Hokkaido System Science Co., Ltd., SEQ ID NO: 31), respectively, to adjust the whole amount of 10 μL. The solutions were reacted at 37° C. for 75 minutes. After the reaction, each solution was adjusted with ultrapure water to 200 μL and measured at an excitation wavelength of 485 nm and an absorption wavelength of 535 nm using infinite F200 (manufactured by TECAN Trading AG) (FIG. 6). For controls, six solutions each containing a mixture of 1 μL of 2 μM 5' miR171-responsive EGFP, 1 μL of ultrapure water, 5 μL of Solution A, and 2 μL of Solution B were prepared and supplemented with 1 μL each of 40 μM and 10 μM synthesized miRNA170 (Hokkaido System Science Co., Ltd., SEQ ID NO: 30), miRNA163, or miRNA164, respectively, to adjust the whole amount of 10 μL. The solutions were reacted at 37° C. for 75 minutes. After the reaction, each solution was adjusted with ultrapure water to 200 μL and measured at an excitation wavelength of 485 nm and an absorption wavelength of 535 nm using infinite F200 (TECAN Trading AG) (FIG. 6). This assay demonstrated that this RNA-responsive artificial RNA switch (5' miR171-responsive EGFP) specifically reacts with miRNA171 and exhibits different translational efficiency even for miRNA170 differing therefrom only by 2 bases.

[Assay on 5' miR170-Responsive EGFP]

Figure 7:
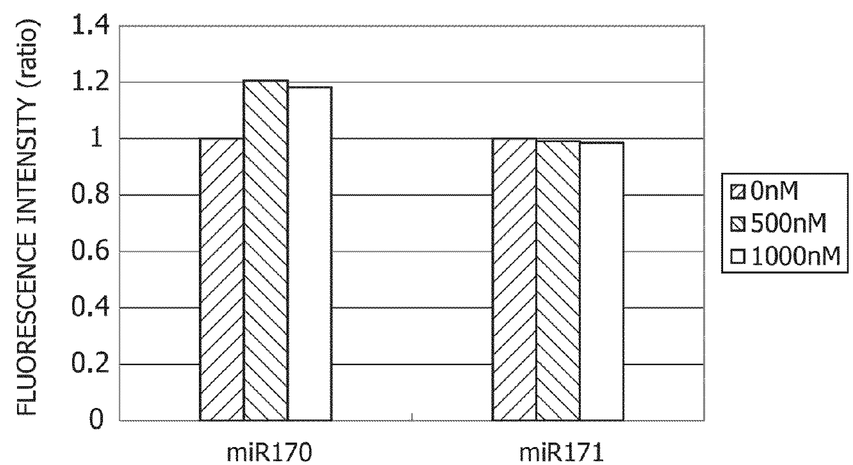
FIG. 7 is a graph showing assay on 5' miR170-responsive EGFP.

Three solutions each containing a mixture of 1 μL of 2 μM 5' miR170-responsive EGFP, 1 μL of ultrapure water, 5 μL of Solution A, and 2 μL of Solution B were prepared and supplemented with 1 μL each of 10 μM, 5 μM, and 0 μM miRNA170, respectively, to adjust the whole amount of 10 μL. The solutions were reacted at 37° C. for 75 minutes. After the reaction, each solution was adjusted with ultrapure water to 200 μL and measured at an excitation wavelength of 485 nm and an absorption wavelength of 535 nm using infinite F200 (manufactured by TECAN Trading AG) (FIG. 7). For controls, three solutions each containing a mixture of 1 μL of 2 μM 5' miR170-responsive EGFP, 1 μL of ultrapure water, 5 μL of Solution A, and 2 μL of Solution B were prepared and supplemented with 1 μL each of 10 μM, 5 μM, and 0 μM synthesized miRNA171, respectively, to adjust the whole amount of 10 μL. The solutions were reacted at 37° C. for 75 minutes. After the reaction, each solution was adjusted with ultrapure water to 200 μL and measured at an excitation wavelength of 485 nm and an absorption wavelength of 535 nm using infinite F200 (manufactured by TECAN Trading AG) (FIG. 7). This assay demonstrated that this RNA-responsive artificial RNA switch (5' miR170-responsive EGFP) specifically reacts with miRNA170 and exhibits different translational efficiency even for miRNA171 differing therefrom only by 2 bases.

Example 3

[Preparation of Liposome Comprising Gene and Cell-Free Expression System Encapsulated Therein and Confirmation of Expression]

[Method for Preparing Liposome Comprising Gene and Cell-Free Expression System Encapsulated Therein]

Figure 8:
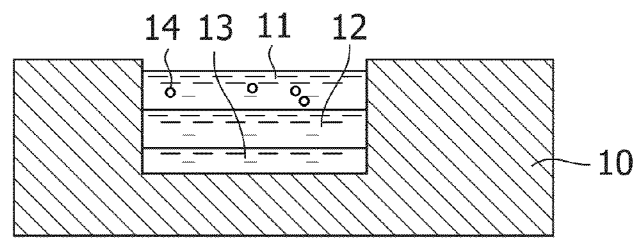
FIG. 8 is a schematic diagram showing the formation of a liposome in a PDMS chamber.
Figure 9:
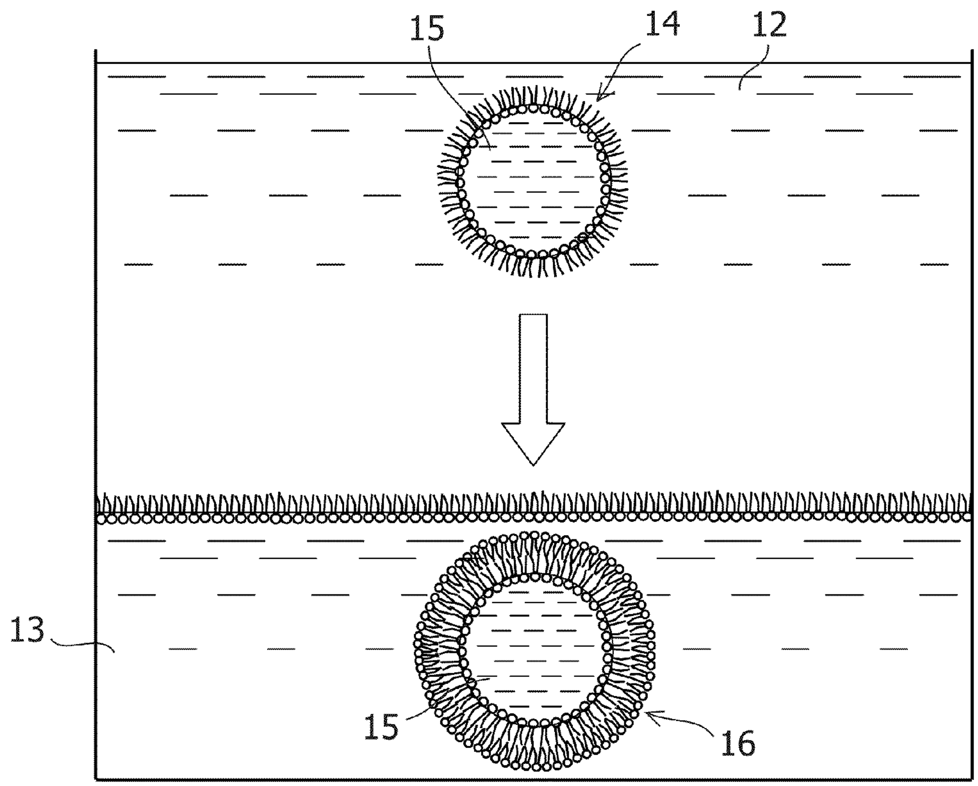
FIG. 9 is a diagram schematically showing the formation of a liposome.

L-α-Phosphatidyl choline (Egg, Chicken) (manufactured by Avanti Polar Lipids, Inc. Polar Lipids, Inc.) was dissolved in a methanol:chloroform=1:2 solution to prepare a 10 mM organic solution of egg PC. 25 to 37.5 μL aliquots of the 10 mM egg PC solution were separately placed in Durham tubes (manufactured by Maruemu Corp.), and the methanol:chloroform solution was evaporated by the spray of nitrogen gas (manufactured by Taiyo Nippon Sanso Corp.) to form lipid films. Each Durham tube with the lipid films thus formed was wrapped in aluminum foil and placed in a desiccator, to which the vacuum was then applied for 10 minutes using a diaphragm dry vacuum pump DA-40S (manufactured by ULVAC, Inc.). Then, 500 μL of mineral oil (manufactured by Nacalai Tesque, Inc.) was added thereto, and the tube was sealed with Parafilm and sonicated at 50° C. for 60 minutes using an ultrasonic cleaner US-1KS (manufactured by SND Co., Ltd.). Immediately after the sonication, the tube was shaken for 20 seconds by vortexing. 0.5 to 0.75 mM egg PC solutions were thus prepared. PDMS was used as a chamber for microscopic observation. FIG. 8 schematically shows the chamber. In FIG. 8, 10 μL of Feeding solution 13 (the details will be described later) was placed in a hole of a PDMS chamber 10 loaded in a cover glass. Then, 10 μL of the egg PC solution 12 thus prepared was gently applied thereonto and left standing for 1 hour. 2.5 μL of Liposome inside solution 15 (the details will be described later) was added to 50 μL of egg PC solution 11, and a W/O emulsion was formed by pipetting. The emulsion 14 was applied onto the Feeding solution-egg PC solution thus left standing to form a liposome 16 (FIG. 9). The PDMS chamber was transferred for observation onto a confocal laser scanning microscope LSM510 (Carl Zeiss Microimaging Inc.) equipped with Thermo Plate (TOKAI HIT COMPANY) set to 37° C.

[Study on Conditions for Feeding Solution and Liposome Inside Solution]

Change in liposome formation ability and in intraliposomal translational efficiency depending on the difference in osmotic pressure between Feeding solution and Liposome inside solution was studied by comparison among a total of 6 combinations involving 3 kinds of Feeding solutions and 2 kinds of Liposome inside solutions. These 3 kinds of Feeding solutions were prepared as (A) Solution A 9.6 μL+Pure mix (mixture of Solution A 5 μL+Solution B 2 μL+ultrapure water 3 μL) 0.4 μL, (B) Solution A 5 μL+ultrapure water 5 μL, and (C) Solution A 5 μL+ultrapure water 4.6 μL+Pure mix 0.4 μL.

Each Feeding solution has the following buffer concentration:

(A) 98 mM Hepes-KOH (pH 7.6), 196 mM L-Glutamic acid Monopotassium salt, 3.92 mM spermidine, 25.48 mM $Mg(OAc)_2$, 1.96 mM DTT, (B) 50 mM Hepes-KOH (pH 7.6), 100 mM L-Glutamic acid Monopotassium salt, 2 mM spermidine, 13 mM $Mg(OAc)_2$, 1 mM DTT, and (C) 52 mM Hepes-KOH (pH 7.6), 104 mM L-Glutamic acid Monopotassium salt, 2.08 mM spermidine, 13.52 mM $Mg(OAc)_2$, 1.04 mM DTT.

The 2 kinds of Liposome inside solutions were prepared as

1. Pure (2 μg/μL Original EGFP template DNA 1 μL+ultrapure water 2 μL+Solution A 5 μL+Solution B 2 μL) 100%, and 2. Pure (2 μg/μL Original EGFP template DNA 1 μL+ultrapure water 2 μL+Solution A 5 μL+Solution B 2 μL) 50%+2-fold diluted Solution A 50% (ultrapure water 5 μL+Solution A 5 μL) 50%.

Each Liposome inside solution has the following buffer concentration:

1. 50 mM Hepes-KOH (pH 7.6), 100 mM L-Glutamic acid Monopotassium salt, 2 mM spermidine, 13 mM $Mg(OAc)_2$, 1 mM DTT, and 2. 50 mM Hepes-KOH (pH 7.6), 100 mM L-Glutamic acid Monopotassium salt, 2 mM spermidine, 13 mM $Mg(OAc)_2$, 1 mM DTT.

First, to compare liposome formation ability, these 2 kinds of Liposome inside solutions were incubated, for EGFP expression, at 37° C. in advance before liposome formation, and liposomes were then prepared. The 3 kinds of Feeding solutions and a 0.5 mM egg PC solution were used. The results demonstrated that a larger number of larger liposomes can be formed by preparation using the Feeding solution (B) or (C) Solution A 5 μL+ultrapure water 4.6 μL+Pure mix 0.4 μL than using the Feeding solution (A) having high osmotic pressure.

Figure 10A:
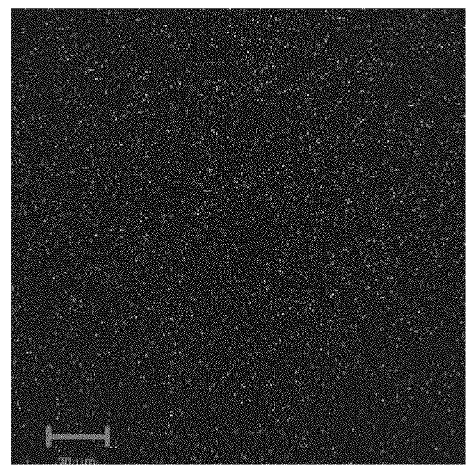
FIG. 10A is a photograph showing fluorescence (fluorescent is absent) within DNA-unencapsulated liposomes.
Figure 10B:
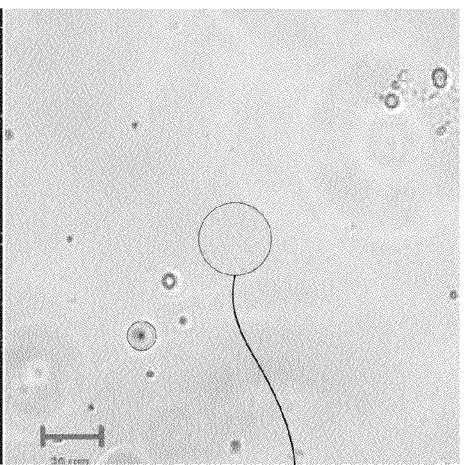
FIG. 10B is a phase-contrast microscopic photograph showing that the liposomes are stably present, wherein the DNA-unencapsulated liposomes were left standing for 1 hour in advance.
Figure 11A:
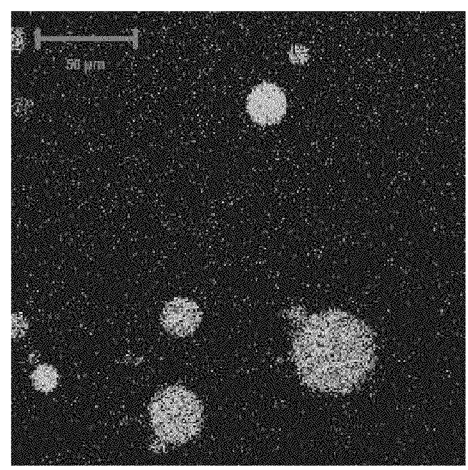
FIG. 11(A) is a photograph showing fluorescence within liposomes in which an EGFP-encoding DNA was encapsulated.
Figure 11B:
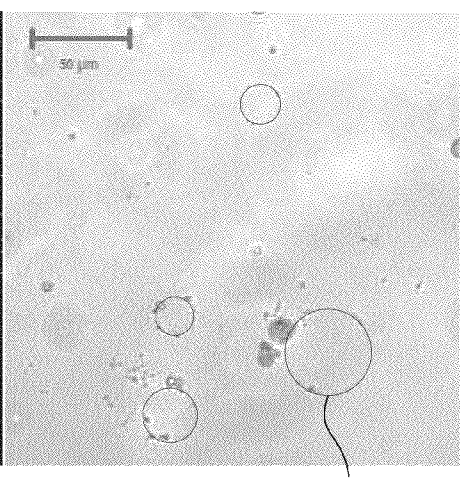
FIG. 11B is a phase-contrast microscopic photograph showing that the liposomes are present, wherein the DNA-encapsulated liposomes were confirmed 1 hour after the encapsulation to have intraliposomal EGFP expression.

Next, an EGFP-encoding DNA was encapsulated in liposomes under conditions involving Feeding solution (A) and Liposome inside solution 2, and 1 hour later, EGFP expression within the liposomes was confirmed. FIG. 11(A) is a photograph showing fluorescence within the liposomes, and FIG. 11(B) is a bright-field microscopic image showing that the liposomes 16 are present. DNA-free liposomes were also stably present after 1 hour (FIG. 10(B)) but do not emit fluorescence (FIG. 10(A)). In FIGS. 10(B) and 11(B), the liposomes were contoured for clearly showing their outlines.

Figure 12:
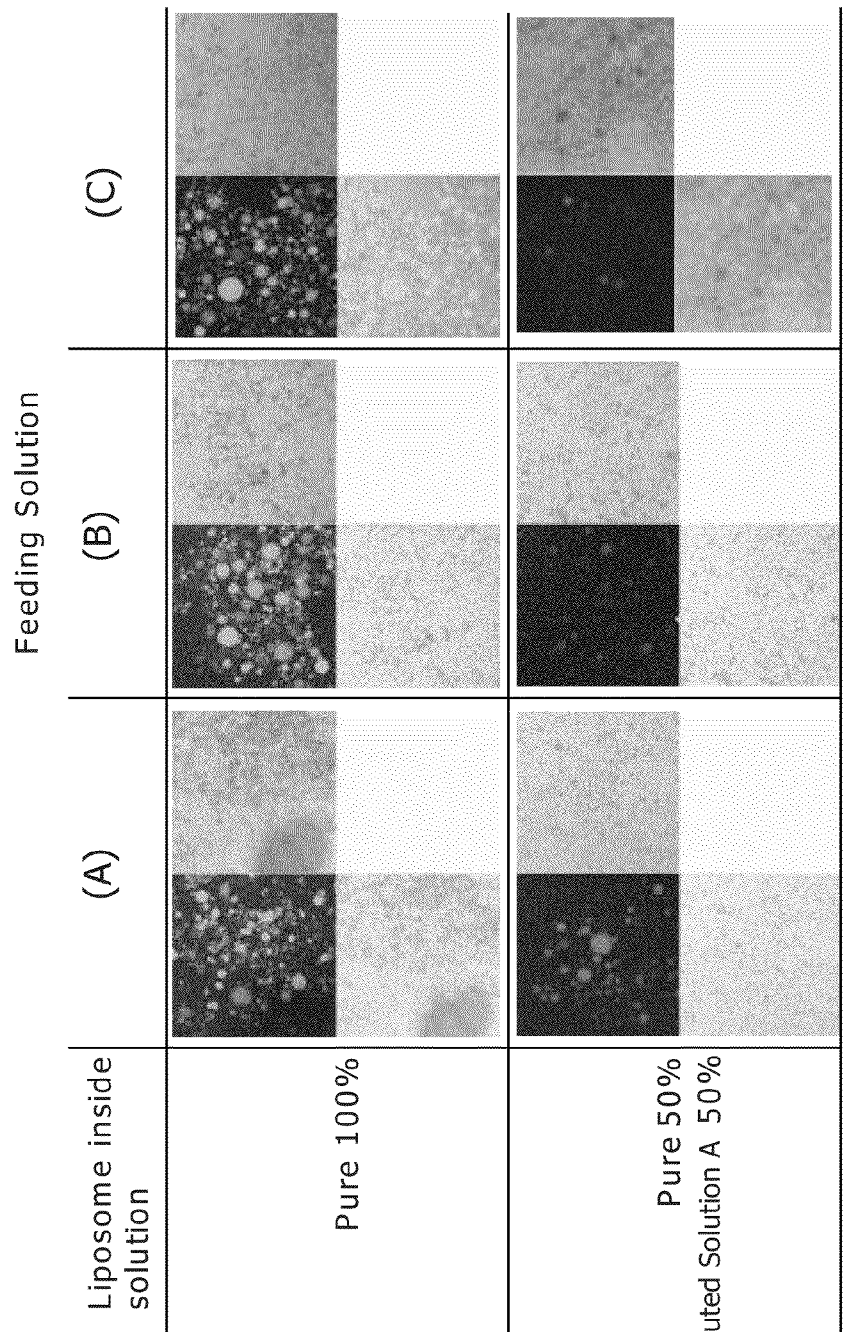
FIG. 12 is a microscopic photograph after liposome formation using 3 kinds of Feeding solutions, a 0.5 mM egg PC solution, and 2 kinds of Liposome inside solutions and subsequent incubation at 37.degree. C. for 60 minutes.

Next, to confirm difference in intraliposomal translational efficiency, the 3 kinds of Feeding solutions, a 0.5 mM egg PC solution, and the 2 kinds of Liposome inside solutions were used to form liposomes, which were then incubated at 37° C. A microscopic photograph after 60 minutes is shown in FIG. 12. As a result, of the two kinds of Liposome inside solutions, Pure 100% offered larger fluorescence intensity. Of the 3 kinds of Feeding Solutions, the Feeding solution (A) offered larger fluorescence intensity than that offered by the other Feeding solutions (B) and (C). However, in terms of the number or size of the liposomes, a larger number of larger liposomes were formed using the Feeding solution (B) or (C) than using the Feeding solution (A), as in the results described above.

In consideration of these results, it was determined that (C) Solution A 5 μL+ultrapure water 4.6 μL+Pure mix 0.4 μL was used as Feeding solution while 1. Pure 100% was used as Liposome inside solution.

[Confirmation of Intraliposomal Original EGFP Template Expression Based on Time Lapse]

First, Original EGFP was used to confirm that time-lapse gene expression necessary for analyzing the efficiency, duration, or the like of an RNA-responsive artificial RNA switch can be achieved intraliposomally. (C) Solution A 5 μL+ultrapure water 4.6 μL+Pure mix 0.4 μL was used as Feeding solution. An egg PC solution was used at a concentration of 0.75 mM. 1. Pure 100% was used as Liposome inside solution. The results are shown in FIG. 13. As is evident therefrom, intraliposomal fluorescence that was not observed at 0 min was observed more brightly and more clearly with a lapse of 15 minutes and distinctly observed at 135 min. These results demonstrated that time-lapse expression can be achieved intraliposomally.

Example 4

[Confirmation of Intraliposomal Translational Regulation of RNA-Responsive Artificial RNA Switch]

[Time-Lapse Intraliposomal Translational Regulation of 5' miR164-Responsive EGFP]

It was confirmed based on time lapse that the translational regulation of 5' miR164-responsive EGFP as an RNA-responsive artificial RNA switch can be achieved intraliposomally. (C) Solution A 5 μL+ultrapure water 4.6 μL+Pure mix 0.4 μL was used as Feeding solution. An egg PC solution was used at a concentration of 0.75 mM. 30 μM 5' miR164-responsive EGFP 1 μL+60 μM miRNA164 1 μL+ultrapure water 1 μL+Solution A 5 μL+Solution B 2 μL was used as Liposome inside solution. The results are shown in FIG. 14. In the drawing, intraliposomal fluorescence was not observed at 0 min, whereas distinct fluorescence could be observed at 60 min. This means that gene translation was switched ON depending on the presence of the miRNA to form the fluorescent protein. These results demonstrated that the translational regulation of the RNA-responsive artificial RNA switch can be achieved intraliposomally.

Example 5

RNA-responsive artificial RNA switches as ON switches were prepared and assayed for their translational regulations.

[Preparation of RNA-Responsive Artificial RNA Switches]

5' miR164-responsive EGFP and 5' miR164-responsive DsRed Monomer were prepared in the same way as in Example 1. miR164, an miRNA complementarily binding to each of them, was purchased from Hokkaido System Science Co., Ltd.

5' miR156-responsive EGFP (SEQ ID NO: 32) was prepared in the same way as in Example 1.

Specifically, all template DNAs for artificial RNA switches were prepared by performing twice or three times PCR using Gradient Master Cycler (Eppendorf). All PCR reactions were performed according to the following protocol using KOD-PLUS-(TOYOBO CO., LTD.). 50 μL of PCR reaction solution contained a mixture of 25 ng of template DNA, 1.5 μL of 10 μM each DNA primers, 5 μL of 2 mM dNTPs, 5 μL of 10×KOD-PLUS-buffer ver. 2, 2 μL of 25 mM $MgSO_4$, and 1 μL of KOD-PLUS-DNA polymerase. Reaction was performed by initially performing incubation at 94° C. for 2 minutes and then 20 cycles each involving 94° C. for 15 seconds, 50° C. for 30 seconds, and 68° C. for 1 minute. After the reaction, the reaction solution was subjected to phenol treatment and ethanol precipitation and dissolved in a nondenaturing dye (30% glycerin, 0.075% xylene cyanol, 0.075% bromophenol blue, 69.85% ultrapure water). The band of interest was separated and excised using low melting point agarose SEAPLAQUE GTG AGAROSE (FMC Corp.). The excised agarose fragment was supplemented with 200 μL of TE, then incubated at 65° C. for 30 minutes, and then subjected to 3 phenol treatments, diethyl ether treatment, and ethanol precipitation for DNA purification. The purification product was dissolved in ultrapure water, followed by concentration measurement using DU640 SPECTROPHOTOMETER (Beckman Coulter, Inc.).

Each template DNA thus prepared was used to perform transcription reaction using MEGAscript (trademark) (Ambion, Inc.). The transcription reaction using MEGAscript was performed as follows. 1 μg of template DNA dissolved in ultrapure water, 2 μL of T7 10× Reaction Buffer, 2 μL of T7 ATP Solution (75 mM) (the same recipe for CTP, GTP, and UTP), and 2 μL of T7 Enzyme Mix were mixed and adjusted with ultrapure water to the whole amount of 20 μL. This reaction solution was reacted at 37° C. for 4 hours to overnight. After the reaction, the solution was supplemented with 1 μL of TURBO DNase and incubated at 37° C. for 15 minutes to decompose the template DNA. Each mRNA obtained through the transcription reaction was purified using RNeasy MinElute (trademark) Cleanup Kit (QIAGEN GmbH).

The names of templates and primers used for preparing each RNA will be shown. In the scheme of miRNA EGFP ON switch production, Original EGFP mRNA (SEQ ID NO: 7) was used as a template DNA for 1st PCR. EGFP DNA after 1st PCR was used as a template DNA for 2nd PCR using primers 5' UTR-miRNA156 fwd (5'GGGAGACCACAACGGTTTCCCTCTATCTCCTGTGCTCACTCTCTTCTGTCAAGA AGGAGATATACCAATG-3', SEQ ID NO: 33) and EGFP rev (SEQ ID NO: 3). miRNA156-responsive EGFP DNA after 2nd PCR was used as a template DNA for 3rd PCR using primers T7-stem-loop uni (SEQ ID NO: 10) and EGFP rev (SEQ ID NO: 3).

5' miR156-responsive DsRed Monomer (SEQ ID NO: 34) was also prepared in the same way as above.

In the scheme of this miRNA-responsive DsRed Monomer ON switch production, pDsRed Monomer (Clontech) (SEQ ID NO: 13) was used as a template DNA for 1st PCR using primers DsRed Monomer fwd (SEQ ID NO: 14) and DsRed Monomer rev (SEQ ID NO: 15). DsRed Monomer DNA after 1st PCR was used as a template DNA for 2nd PCR using primers 5' UTR-miRNA156 fwd (SEQ ID NO: 34) and DsRed Monomer rev (SEQ ID NO: 15). miRNA156-responsive DsRed Monomer DNA after 2nd PCR was used as a template DNA for 3rd PCR using primers T7-stem-loop uni (SEQ ID NO: 10) and DsRed Monomer rev (SEQ ID NO: 15).

Moreover, miR156 (5'-UGACAGAAGAGAGUGAGCAC-3', SEQ ID NO: 35), an miRNA complementarily binding to each of 5' miR156-responsive EGFP and 5' miR156-responsive DsRed Monomer was purchased from Hokkaido System Science Co., Ltd.

[Translational Regulation Assay Using Cell-Free Expression System of RNA-Responsive Artificial RNA Switch]

2000 nM each RNA-responsive artificial RNA switches thus prepared were supplemented with each miRNA complementarily binding to each RNA-responsive artificial RNA switch, and EGFP and DsRed Monomer proteins were expressed in the PURE system and confirmed for their fluorescence intensities using each filter. The ratio of change in fluorescence intensity was plotted against change in the concentration of each miRNA when the fluorescence intensity of each protein obtained without the miRNA addition is defined as 1.

Figure 21:
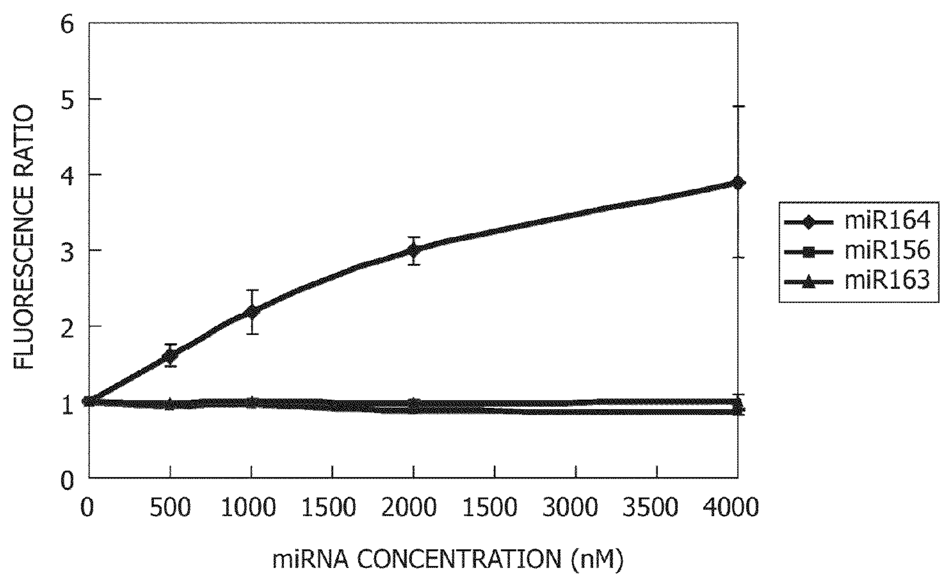
FIG. 21 is a graph showing assay on a 5' miR164-responsive EGFP switch.
Figure 22:
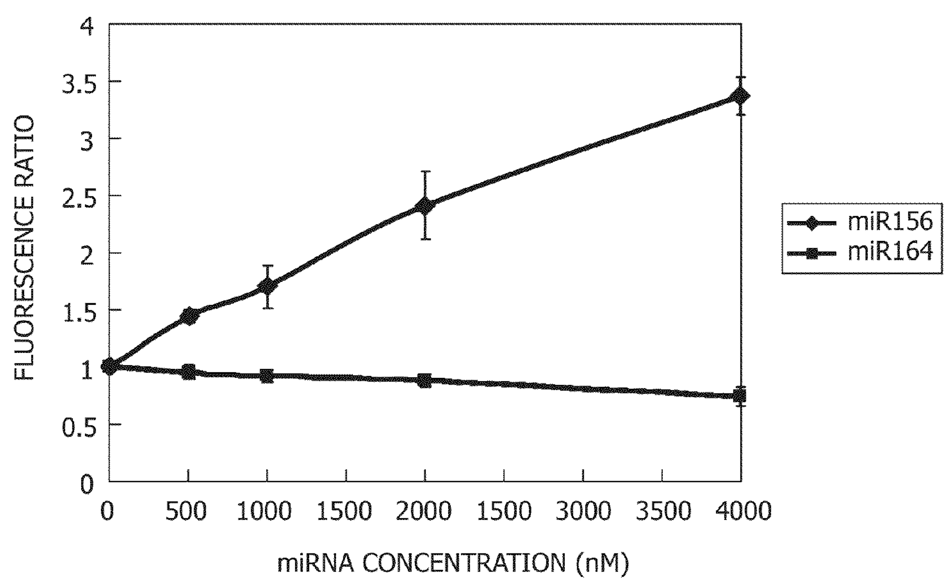
FIG. 22 is a graph showing assay on a 5' miR156-responsive EGFP switch.
Figure 23:
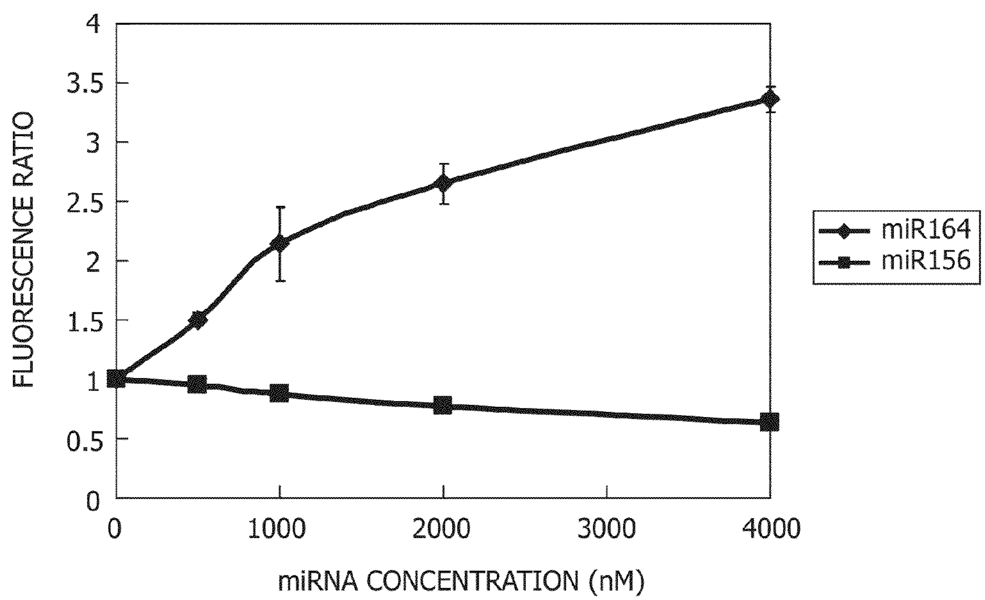
FIG. 23 is a graph showing assay on a 5' miR164-responsive DsRed Monomer switch.
Figure 24:
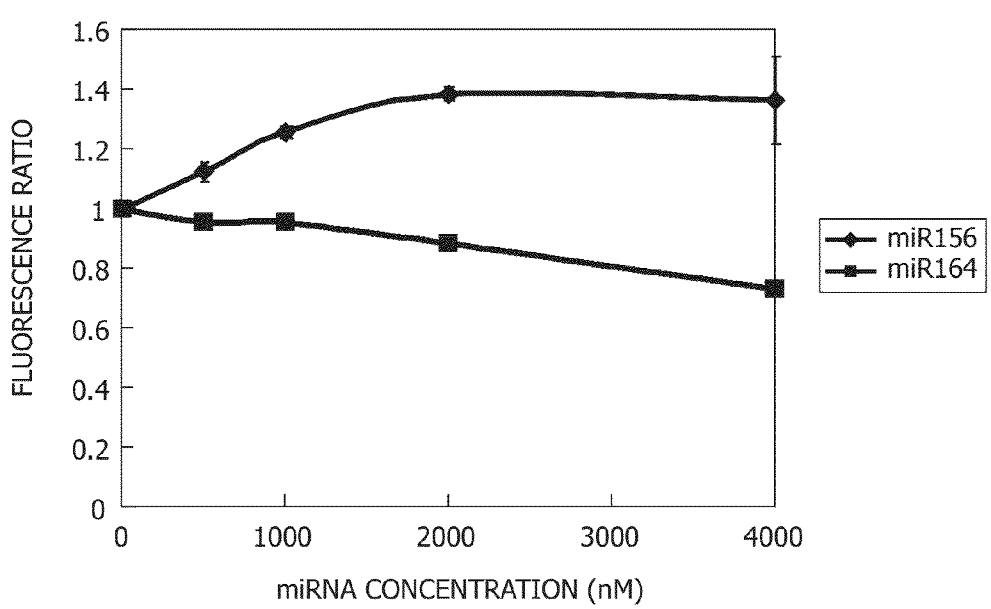
FIG. 24 is a graph showing assay on a 5' miR156-responsive DsRed Monomer switch.

FIG. 21 is a graph of plotting the ratio of change in fluorescence intensity against each concentration of miR164, miR156, or miR163 added to the 5' miR164-responsive EGFP switch. FIG. 22 is a graph of plotting the ratio of change in fluorescence intensity against each concentration of miR156 or miR164 added to the 5' miR156-responsive EGFP switch. FIG. 23 is a graph of plotting the ratio of change in fluorescence intensity against each concentration of miR164 or miR156 added to the 5' miR164-responsive DsRed Monomer switch. FIG. 24 is a graph of plotting the ratio of change in fluorescence intensity against each concentration of miR156 or miR164 added to the 5' miR156-responsive DsRed Monomer switch. As is evident from these results, each switch can specifically recognize only the target miRNA from among miRNAs similar in sequence and length to activate translation. Furthermore, it was revealed that the type of a gene to be translated is independent of a particular sequence and the translational activation of an arbitrary gene can be regulated.

Example 6

[Two Different ON Switch RNAs]

Two RNA-responsive artificial RNA switches that switch ON gene expression in response to different miRNAs were prepared and combined to construct the simplest artificial translational system.

The RNA-responsive artificial RNA switches used were 5' miR164-responsive DsRed Monomer and 5' miR156-responsive EGFP prepared in Example 5. miR164 (SEQ ID NO: 29) and miR156 (SEQ ID NO: 39) were used as miRNAs complementarily binding to each RNA-responsive artificial RNA switch.

Figure 25:
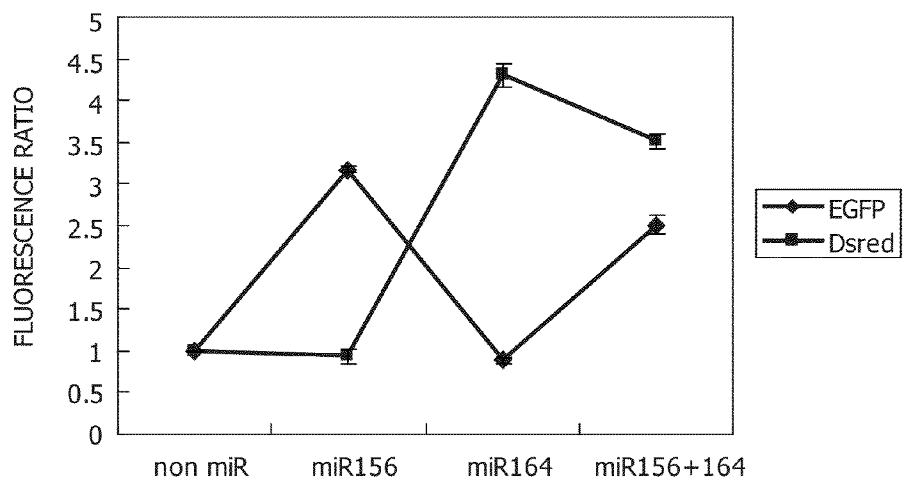
FIG. 25 is a graph showing assay on 5' miR164-responsive DsRed Monomer and 5' miR156-responsive EGFP.

A mixed solution containing 2000 nM each of two RNA-responsive artificial RNA switches was supplemented with 4000 nM each miRNA. Next, EGFP and DsRed Monomer proteins were expressed in the PURE system and confirmed for their fluorescence intensities using each filter. The ratio of change in fluorescence intensity depending on each added miRNA was plotted when the fluorescence intensity of each protein obtained without the miRNA addition is defined as 1. The results are shown in FIG. 25. As is evident from the graph, the addition of miRNA156 caused the green fluorescence of EGFP while the addition of miRNA164 caused the red fluorescence of DsRed Monomer. Thus, the selective emission of green or red fluorescence could be achieved, demonstrating the successful construction of the artificial translational system.

Example 7

[OFF Switch EGFP]

[Design]

Figure 26:
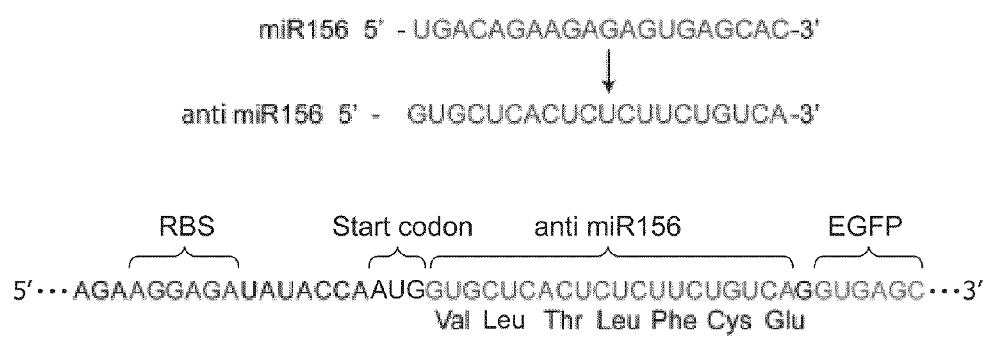
FIG. 26 is a diagram showing miR156 (SEQ ID NO:35), anti miR156 (SEQ ID NO:37), and an miR156-responsive EGFP OFF switch (SEQ ID NO:50; SEQ ID NO:51)
Figure 27:
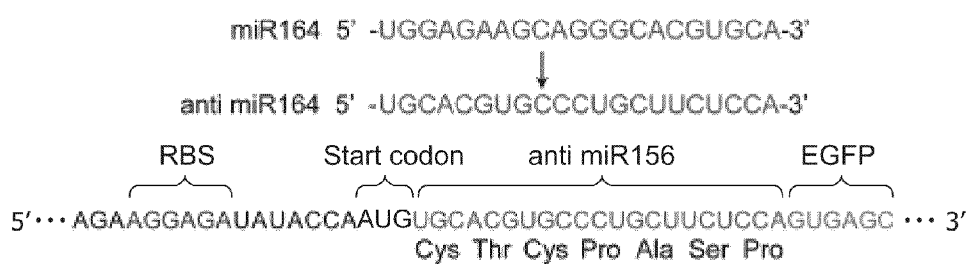
FIG. 27 is a diagram showing miR164 (SEQ ID NO:29), anti miR164 (SEQ ID NO:39), and an miR164-responsive EGFP OFF switch (SEQ ID NO:52; SEQ ID NO:53)

RNA-responsive artificial RNA switches that switch OFF EGFP expression in response to an miRNA were prepared. FIGS. 26 and 27 show the designed RNA-responsive artificial RNA switches, miRNAs specifically binding thereto, and reverse complements of the miRNAs. Moreover, below each RNA-responsive artificial RNA switch, amino acids are shown, which are added to the N terminus of the expressed EGFP by inserting the reverse complement of the miRNA 3' to the start codon and 5' to the EGFP gene. The RNA-responsive artificial RNA switch shown in FIG. 26 is intended to cause EGFP expression in the absence of miRNA156 (SEQ ID NO: 35) and repress EGFP expression in response to miRNA156. This mRNA is referred to as an miR156-responsive EGFP OFF switch (SEQ ID NO: 36). The miR156-responsive EGFP OFF switch contains the sequence of the reverse complement (5'-GUGCUCACUCUCUUCUGUCA-3', SEQ ID NO: 37) of miRNA156.

The RNA-responsive artificial RNA switch shown in FIG. 27 is intended to cause EGFP expression in the absence of miRNA164 (SEQ ID NO: 29) and repress EGFP expression in response to miRNA164. This mRNA is referred to as an miR164-responsive EGFP OFF switch (SEQ ID NO: 38). The miR164-responsive EGFP OFF switch contains the sequence of the reverse complement (5'-UGCACGUGCCCUGCUUCUCCA-3', SEQ ID NO: 39) of miRNA164.

[Production]

All template DNAs for artificial RNA switches were prepared by performing twice or three times PCR using Gradient Master Cycler (Eppendorf). All PCR reactions were performed according to the following protocol using KOD-PLUS-(TOYOBO CO., LTD.). 50 μL of PCR reaction solution contained a mixture of 25 ng of template DNA, 1.5 μL of 10 μM each DNA primers, 5 μL of 2 mM dNTPs, 5 μL of 10×KOD-PLUS-buffer ver. 2, 2 μL of 25 mM $MgSO_4$, and 1 μL of KOD-PLUS-DNA polymerase. Reaction was performed by initially performing incubation at 94° C. for 2 minutes and then 20 cycles each involving 94° C. for 15 seconds, 50° C. for 30 seconds, and 68° C. for 1 minute. After the reaction, the reaction solution was subjected to phenol treatment and ethanol precipitation and dissolved in a nondenaturing dye (30% glycerin, 0.075% xylene cyanol, 0.075% bromophenol blue, 69.85% ultrapure water). The band of interest was separated and excised using low melting point agarose SEAPLAQUE GTG AGAROSE (FMC Corp.). The excised agarose fragment was supplemented with 200 μL of TE, then incubated at 65° C. for 30 minutes, and then subjected to 3 phenol treatments, diethyl ether treatment, and ethanol precipitation for DNA purification. The purification product was dissolved in ultrapure water, followed by concentration measurement using DU640 SPECTROPHOTOMETER (Beckman Coulter, Inc.).

Each template DNA thus prepared was used to perform transcription reaction using MEGAscript (trademark) (Ambion, Inc.). The transcription reaction using MEGAscript was performed as follows. 1 μg of template DNA dissolved in ultrapure water, 2 μL of T7 10× Reaction Buffer, 2 μL of T7 ATP Solution (75 mM) (the same recipe for CTP, GTP, and UTP), and 2 μL of T7 Enzyme Mix were mixed and adjusted with ultrapure water to the whole amount of 20 μL. This reaction solution was reacted at 37° C. for 4 hours to overnight. After the reaction, the solution was supplemented with 1 μL of TURBO DNase and incubated at 37° C. for 15 minutes to decompose the template DNA. Each mRNA obtained through the transcription reaction was purified using RNeasy MinElute (trademark) Cleanup Kit (QIAGEN GmbH).

In the scheme of miRNA-responsive EGFP OFF switch production, pEGFP (Clontech) (SEQ ID NO: 1) was used as a template DNA for 1st PCR using primers miR156-responsive OFF fwd (5'AAGGAGATATACCAATGGTGCTCACTCTCTTCTGTCAGGTGAGCAAGGGCGAG GAG-3, SEQ ID NO: 40) or miR164-responsive OFF fwd (5'AAGGAGATATACCAATGTGCACGTGCCCTGCTTCTCCAGTGAGCAAGGGCGAG GAG-3', SEQ ID NO: 41) and EGFP rev (SEQ ID NO: 3). EGFP DNA after 1st PCR was used as a template DNA for 2nd PCR using primers Universal primer (SEQ ID NO: 5) and EGFP rev (SEQ ID NO: 3). The miRNA and each primer were purchased from Hokkaido System Science Co., Ltd.

[Evaluation]

The miR156-responsive EGFP OFF switch or the miR164-responsive EGFP OFF switch was supplemented with each concentration of miRNA156 or miRNA164. Their EGFP proteins were expressed in the PURE system and confirmed for their fluorescence intensities. Change in fluorescence ratio was plotted against change in the concentration of each miRNA when the fluorescence intensity obtained without the miRNA addition is defined as 1. The results are shown in the drawings.

Figure 28:
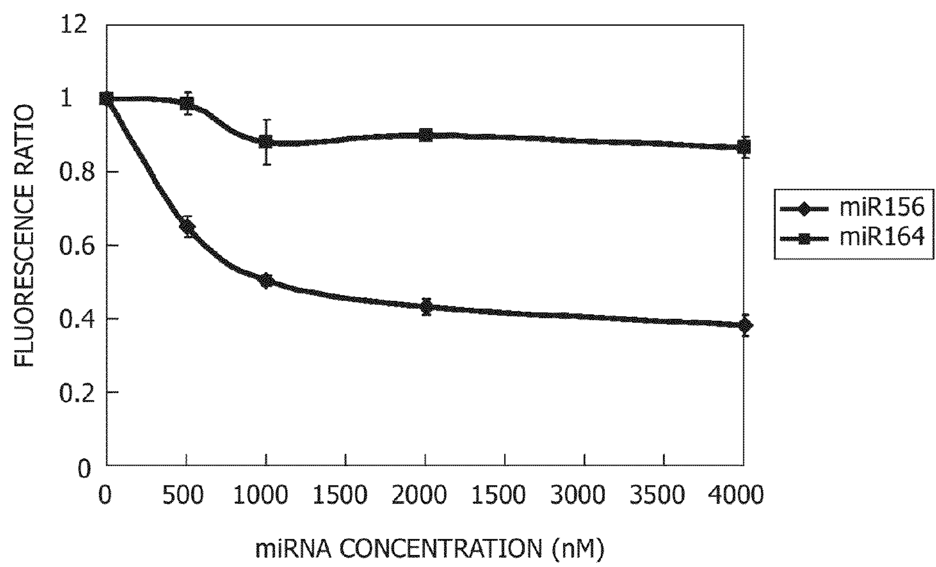
FIG. 28 is a graph showing assay on an miR156-responsive EGFP OFF switch.
Figure 29:
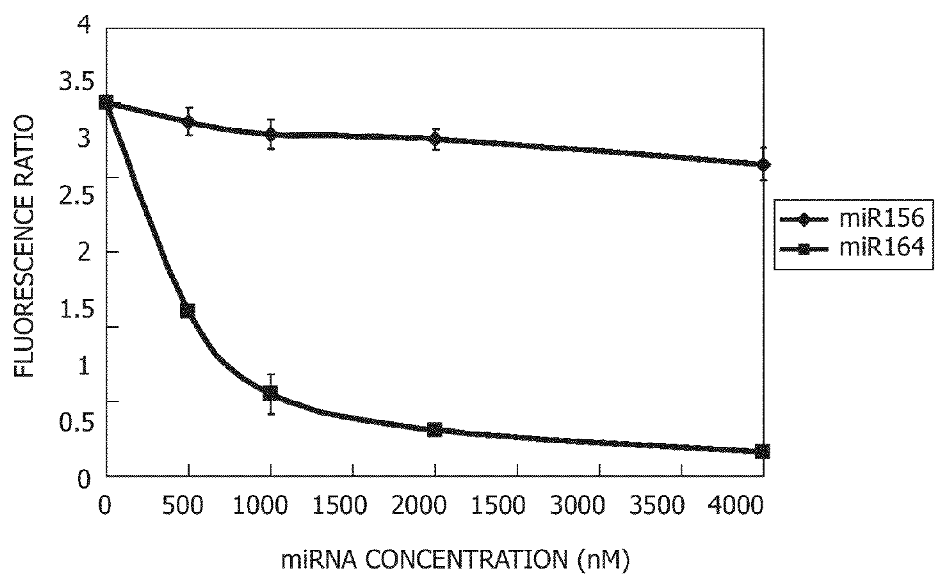
FIG. 29 is a graph showing assay on an miR164-responsive EGFP OFF switch.

FIG. 28 is a graph of plotting the ratio of change in fluorescence intensity against each concentration of miRNA156 or miRNA164 added to 200 nM miR156-responsive EGFP OFF switch. FIG. 29 is a graph of plotting the ratio of change in fluorescence intensity against each concentration of miRNA156 or miRNA164 added to 100 nM miR164-responsive EGFP OFF switch. As is evident from both the graphs, specific translational repression occurred. Moreover, from these results, it was found that even when the reverse complement of the miRNA is inserted immediately downstream of the start codon, the efficiency of expression of EGFP proteins with N-terminally added 7 amino acids is not reduced. This is a dramatic outcome demonstrating that the design of the EGFP OFF switch attained greater success than expected.

[OFF Switch DsRed Monomer]

[Design]

Figure 30:
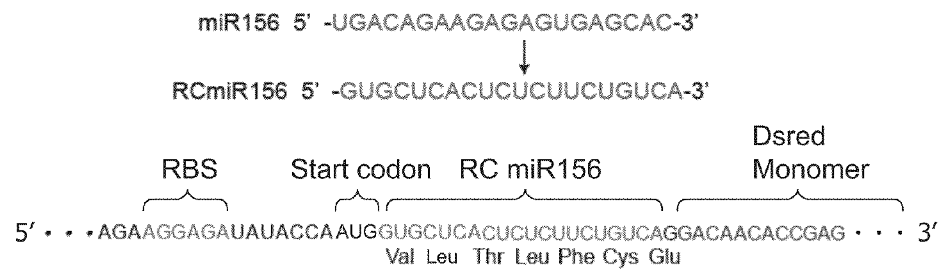
FIG. 30 is a diagram showing miR156 (SEQ ID NO:35), anti miR156 (SEQ ID NO:37), and an miR156-responsive DsRed Monomer OFF switch (SEQ ID NO:54; SEQ ID NO: 51)
Figure 31:
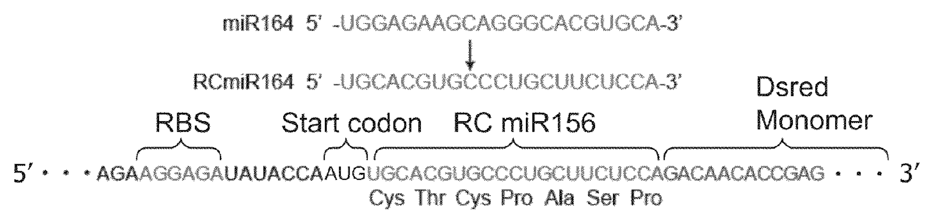
FIG. 31 is a diagram showing miR164 (SEQ ID NO:29), anti miR164 (SEQ ID NO:37), and an miR164-responsive DsRed Monomer OFF switch (SEQ ID NO:55; SEQ ID NO: 53)

RNA-responsive artificial RNA switches that switch OFF DsRed Monomer expression in response to an miRNA were prepared. FIGS. 30 and 31 show the designed RNA-responsive artificial RNA switches, miRNAs specifically binding thereto, and reverse complements of the miRNAs. Moreover, beneath each RNA-responsive artificial RNA switch, amino acids are shown, which are added to the N terminus of the expressed DsRed Monomer by inserting the reverse complement of the miRNA 3' to the start codon and 5' to the DsRed Monomer gene. The RNA-responsive artificial RNA switch shown in FIG. 30 is intended to cause DsRed Monomer expression in the absence of miRNA156 and repress DsRed Monomer expression in response to miRNA156. This mRNA is referred to as an miR156-responsive DsRed Monomer OFF switch RNA (SEQ ID NO: 42). The RNA-responsive artificial RNA switch shown in FIG. 31 is intended to cause DsRed Monomer expression in the absence of miRNA164 and repress DsRed Monomer expression in response to miRNA164. This mRNA is referred to as an miR164-responsive DsRed Monomer OFF switch RNA (SEQ ID NO: 43).

[Production]

The miR156-responsive DsRed Monomer OFF switch and the miR164-responsive DsRed Monomer OFF switch were produced in the same way as in the OFF switch EGFP.

pDsRed Monomer (Clontech) (SEQ ID NO: 13) was used as a template DNA for 1st PCR using primers miR156-responsive OFF fwd (SEQ ID NO: 40) or miR164-responsive OFF fwd (SEQ ID NO: 41) and DsRed Monomer rev (SEQ ID NO: 16). DsRed Monomer DNA after 1st PCR was used as a template DNA for 2nd PCR using primers Universal primer (SEQ ID NO: 5) and DsRed Monomer rev (SEQ ID NO: 16).

[Evaluation]

200 nM each miR156-responsive DsRed Monomer OFF switch or 200 nM miR164-responsive DsRed Monomer OFF switch was supplemented with each concentration of miRNA156 or miRNA164. Their EGFP proteins were expressed in the PURE system and confirmed for their fluorescence intensities. Change in fluorescence ratio was plotted against change in the concentration of each miRNA when the fluorescence intensity obtained without the miRNA addition is defined as 1. The results are shown in the drawings.

Figure 32:
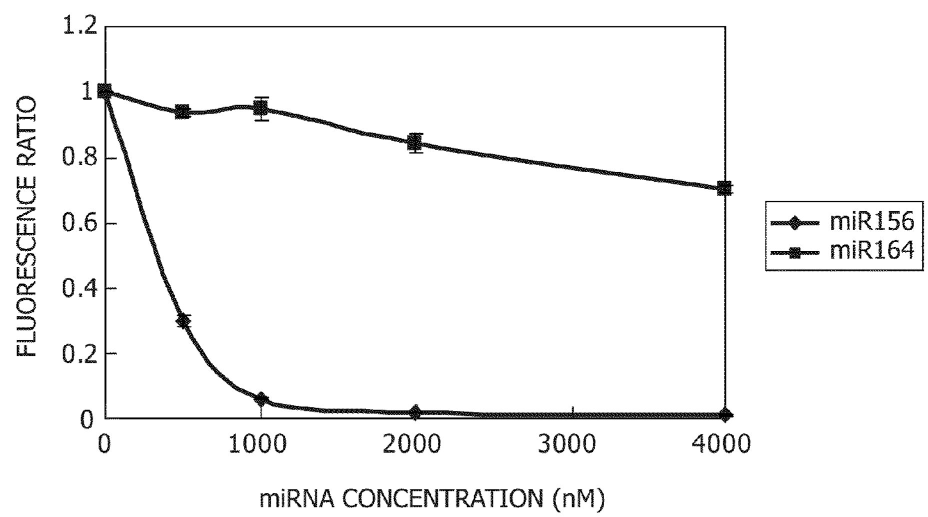
FIG. 32 is a graph showing assay on an miR156-responsive DsRed Monomer OFF switch.
Figure 33:
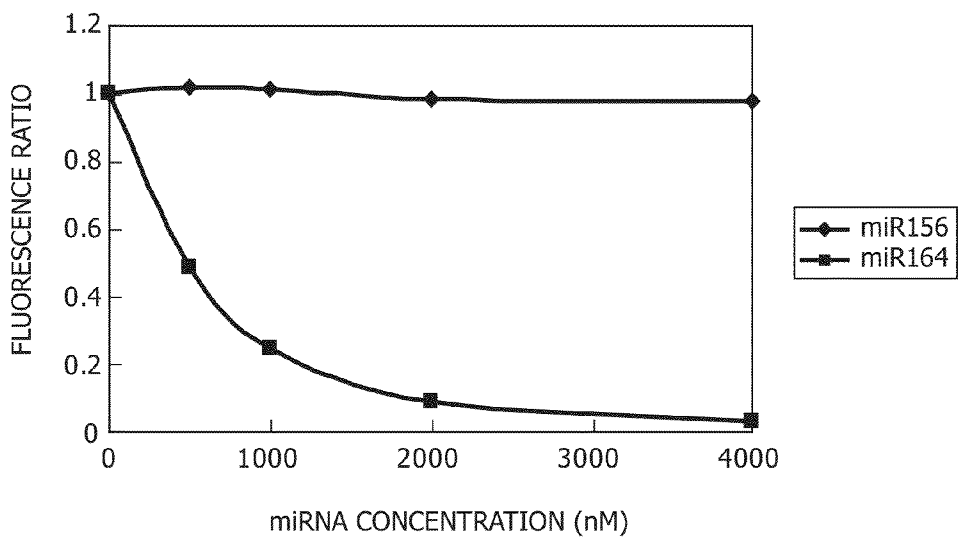
FIG. 33 is a graph showing assay on an miR164-responsive DsRed Monomer OFF switch.

FIG. 32 is a graph of plotting the ratio of change in fluorescence intensity against each concentration of miRNA156 or miRNA164 added to 200 nM miR156-responsive DsRed Monomer OFF switch. FIG. 33 is a graph of plotting the ratio of change in fluorescence intensity against each concentration of miRNA156 or miRNA164 added to 200 nM miR164-responsive DsRed Monomer OFF switch. As is evident from both the graphs, specific translational repression occurred. In this case as well, the reverse complement of the miRNA inserted immediately downstream of the start codon has a little influence on the efficiency of DsRed Monomer expression, as in EGFP, demonstrating that the OFF switch was successfully designed efficiently.

Example 8

[Artificial Translational System Using Different Switches Responding to the Same Small RNA]

[From Green to Red]

An artificial translational system using different switches responding to the same small RNA was evaluated. An miR164-responsive EGFP OFF switch (FIG. 27) that regulates EGFP expression in an ON-to-OFF manner in response to miR164 was prepared according to Example 7. An miR164-responsive DsRed Monomer ON switch (SEQ ID NO: 19) that regulates DsRed Monomer expression in an OFF-to-ON manner in response to miR164 was prepared according to Example 1.

Figure 34:
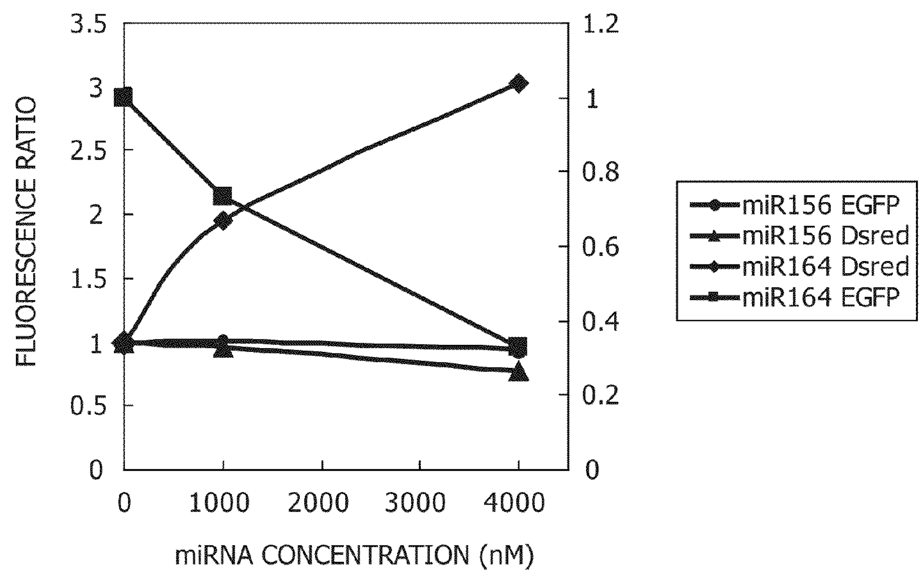
FIG. 34 is a graph showing assay on an miR164-responsive EGFP OFF switch and an miR164-responsive DsRed Monomer ON switch.

A mixed solution of 100 nM miR164-responsive EGFP OFF switch and 2000 nM miR164-responsive DsRed Monomer ON switch was supplemented with each concentration of miR156 or miR164, and EGFP and DsRed Monomer proteins were expressed in the PURE system and confirmed for their fluorescence intensities using each filter. The ratio of change in fluorescence intensity was plotted against change in the concentration of each miRNA when the fluorescence intensity of each protein obtained without the miRNA addition is defined as 1. The results are shown in FIG. 34. In the graph of FIG. 34, the left scales relate to miR156 EGFP, miR156 DsRed, and miR164 DsRed, and the right scales relate to miR164 EGFP. In this context, miR156 EGFP represents the fluorescence ratio of EGFP obtained by the addition of miR156; miR156 DsRed represents the fluorescence ratio of DsRed obtained by the addition of miR156; miR164 EGFP represents the fluorescence ratio of EGFP obtained by the addition of miR164; and miR164 DsRed represents the fluorescence ratio of DsRed obtained by the addition of miR164. miR164-specific change from green to red colors could be confirmed, demonstrating that the artificial translational system was successfully constructed. Moreover, the absence of change in fluorescence caused by miRNA156 was used as a control.

[From Red to Green]

Other artificial translational systems using different switches responding to the same small RNA were evaluated.

A 5' miR156-responsive EGFP ON switch that regulates EGFP expression in an OFF-to-ON manner in response to miR156 was prepared according to Example 5. On the other hand, an miR156-responsive DsRed Monomer OFF switch (FIG. 30) that regulates DsRed Monomer expression in an ON-to-OFF manner in response to miR156 was prepared according to Example 7.

Figure 35:
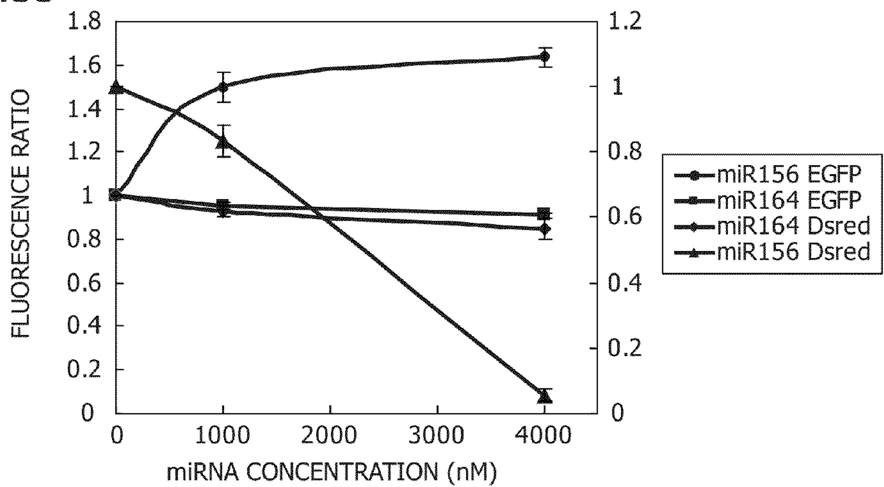
FIG. 35 is a graph showing assay on a 5' miR156-responsive EGFP ON switch and an miR156-responsive DsRed Monomer OFF switch supplemented with each concentration of miR156 or miR164.

A mixed solution of 2000 nM 5' miR156-responsive EGFP ON switch and 500 nM miR156-responsive DsRed Monomer OFF switch was supplemented with each concentration of miR156 or miR164, and EGFP and DsRed Monomer proteins were expressed in the PURE system and confirmed for their fluorescence intensities using each filter. The ratio of change in fluorescence intensity was plotted against change in the concentration of each miRNA when the fluorescence intensity of each protein obtained without the miRNA addition is defined as 1. The results are shown in FIG. 35. In the graph of FIG. 35, the left scales relate to miR156 EGFP, miR164 EGFP, and miR164 DsRed, and the right scales relate to miR156 DsRed. miR156-specific change from red to green colors could be confirmed, demonstrating that the artificial translational system was successfully constructed. Moreover, the absence of change in fluorescence caused by miRNA164 was used as a control.

A 5' miR164-responsive EGFP ON switch that regulates EGFP expression in an OFF-to-ON manner in response to miR164 was prepared according to Example 1. On the other hand, an miR164-responsive DsRed Monomer OFF switch (FIG. 31) that regulates DsRed Monomer expression in an ON-to-OFF manner in response to miR164 was prepared according to Example 7.

Figure 36:
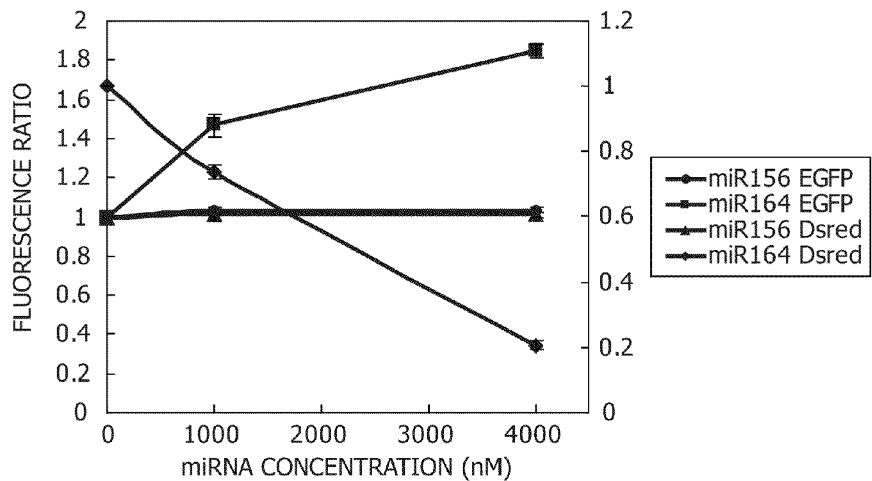
FIG. 36 is a graph showing assay on a 5' miR164-responsive EGFP ON switch and an miR164-responsive DsRed Monomer OFF switch supplemented with each concentration of miR164 or miR156.

A mixed solution of 2000 nM 5' miR164-responsive EGFP ON switch and 500 nM miR164-responsive DsRed Monomer OFF switch was supplemented with each concentration of miR156 or miR164, and EGFP and DsRed Monomer proteins were expressed in the PURE system and confirmed for their fluorescence intensities using each filter. The ratio of change in fluorescence intensity was plotted against change in the concentration of each miRNA when the fluorescence intensity of each protein obtained without the miRNA addition is defined as 1. The results are shown in FIG. 36. In the graph of FIG. 36, the left scales relate to miR156 EGFP, miR164 EGFP, and miR156 DsRed, and the right scales relate to miR164 DsRed. miR164-specific change from red to green colors could be confirmed, demonstrating that the artificial translational system was successfully constructed. Moreover, the absence of change in fluorescence caused by miRNA156 was used as a control.

Example 9

[Double ON Switch]

[Preparation of RNA-Responsive Artificial RNA (miRNA159a-Responsive EGFP on Switch)]

Figure 37:
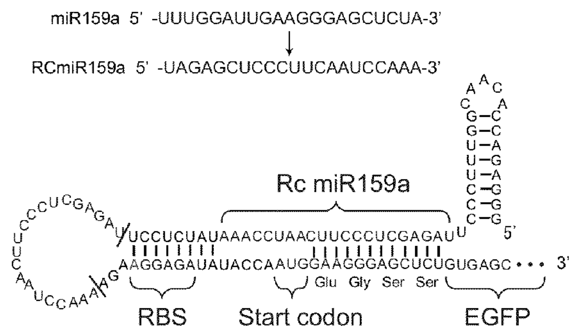
FIG. 37 is a diagram showing miRNA159a (SEQ ID NO:44), RCmiRNA159a (SEQ ID NO:45), and the secondary structure of an miRNA159a-responsive EGFP ON switch as a double ON switch mRNA (SEQ ID NO: 56; SEQ ID NO:57)

An RNA-responsive artificial RNA (miRNA159a-responsive EGFP ON switch) was prepared in the same way as in Example 1. FIG. 37 shows miRNA159a (5'-UUUGGA-UUGAAGGGAGCUCUA-3', SEQ ID NO: 44), its complementary strand (5'-UAGAGCUCCCUUCAAUCCAAA-3', SEQ ID NO: 45), and the secondary structure of a double ON switch mRNA (SEQ ID NO: 46) specifically reacting with miRNA159a.

[Preparation of RNA-Responsive Artificial RNA (miRNA163-Responsive EGFP ON Switch)]

Figure 38:
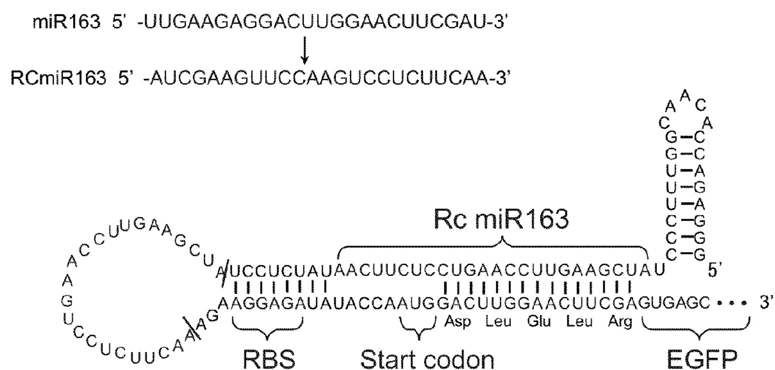
FIG. 38 is a diagram showing miRNA163 (SEQ ID NO:28), RCmiRNA163 (SEQ ID NO:47), and the secondary structure of an miRNA163-responsive EGFP ON switch as a double ON switch mRNA (SEQ ID NO:58, SEQ ID NO:59)

An RNA-responsive artificial RNA (miRNA163-responsive EGFP ON switch) was prepared in the same way as in Example 1. FIG. 38 shows miRNA163 (SEQ ID NO: 28), its complementary strand (5'-AUCGAAGUUCCAAGUCCU-CUUCAA-3', SEQ ID NO: 47), and the secondary structure of a double ON switch mRNA (SEQ ID NO: 48) specifically reacting with miRNA163.

[Translational Regulation Assay Using Cell-Free Expression System of RNA-Responsive Artificial RNA Switch]

A cell-free expression system PURE system was used for confirming the translational regulations of these two RNA-responsive artificial RNA switches. The PURE system is as described in Example 2.

[Assay on miRNA159a-Responsive EGFP ON Switch]

Figure 39:
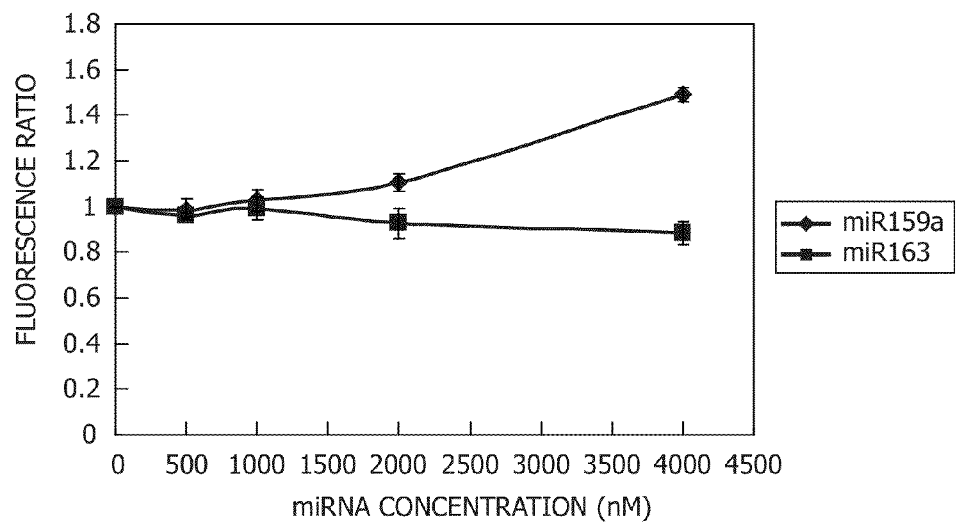
FIG. 39 is a graph showing assay on an miRNA159a-responsive EGFP ON switch.

Five solutions each containing a mixture of 1 μL of 20 μM miRNA159a-responsive EGFP, 1 μL of ultrapure water, 5 μL of Solution A, and 2 μL of Solution B were prepared and supplemented with 1 μL each of 40 μM, 20 μM, 10 μM, 5 μM, and 0 μM synthesized miRNA159a (SEQ ID NO: 44), respectively, to adjust the whole amount of 10 μL. The solutions were reacted at 37° C. for 75 minutes. After the reaction, each solution was adjusted with ultrapure water to 200 μL and measured at an excitation wavelength of 485 nm and an absorption wavelength of 535 nm using infinite F200 (manufactured by TECAN Trading AG) (FIG. 39). For negative controls, five solutions each containing a mixture of 1 μL of 20 μM miRNA159a-responsive EGFP, 1 μL of ultrapure water, 5 μL of Solution A, and 2 μL of Solution B were prepared and supplemented with 1 μL each of 40 μM, 20 μM, 10 μM, 5 μM, and 0 μM synthesized miRNA163 (Hokkaido System Science Co., Ltd., SEQ ID NO: 28), respectively, to adjust the whole amount of 10 μL. The solutions were reacted at 37° C. for 75 minutes. After the reaction, each solution was adjusted with ultrapure water to 200 μL and measured at an excitation wavelength of 485 nm and an absorption wavelength of 535 nm using infinite F200 (TECAN Trading AG) (FIG. 39). This assay demonstrated that this RNA-responsive artificial RNA switch (miRNA159a-responsive EGFP) specifically reacts with miRNA159a to perform OFF-to-ON translational regulation.

[Assay on miRNA163-Responsive EGFP ON Switch]

Figure 40:
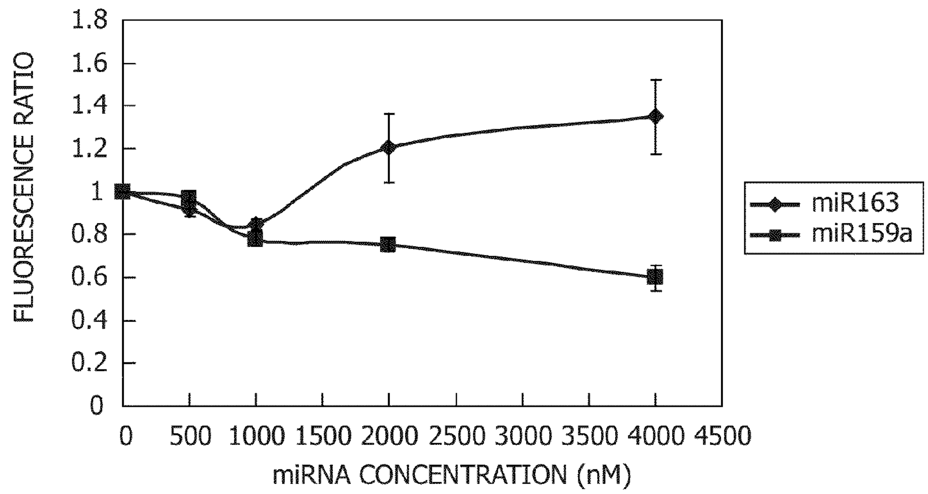
FIG. 40 is a graph showing assay on an miRNA163-responsive EGFP ON switch.

An miRNA163-responsive EGFP ON switch (SEQ ID NO: 48) was assayed in the same way as in the miRNA159a-responsive EGFP. For negative controls, an miRNA163-responsive EGFP ON switch was supplemented with miRNA159a for use. The concentration of the miRNA163-responsive EGFP switch was set to 1 μM. The measurement results are shown in FIG. 40. This assay demonstrated that the miRNA163-responsive EGFP ON switch specifically reacts with miRNA163 to perform OFF-to-ON translational regulation.

INDUSTRIAL APPLICABILITY

In applications, the present invention can function as biosensors or artificial genetic circuits that can regulate the expression of downstream signal proteins (e.g., fluorescent or luminescent proteins) in response to the expression of an arbitrary RNA. By intracellular introduction of this artificial RNA, the present invention can be developed into systems that detect cells expressing a particular RNA (miRNA, etc.) without destroying the cells, or into techniques of regulating the fate of cells.

Moreover, an intraliposomal genetic network can be constructed by encapsulating the artificial RNA together with a cell-free translational system into liposomes.

The invention claimed is:

1. An mRNA comprising a microRNA-binding site located 5' to the ribosome-binding site and a nucleotide sequence located 5' to the microRNA-binding site, the nucleotide sequence being complementary to the ribosome-binding site.

2. The mRNA according to claim 1, wherein the microRNA-binding site has a sequence complementary to a microRNA selected from miR164, miR170, miR171, miR156, miR159a or miR163.

3. A liposome comprising an mRNA according to claim 1 encapsulated therein.

4. The liposome according to claim 3, wherein the liposome is produced by a method comprising steps of:

mixing one or more phospholipids, the mRNA, a cell-free translation system, and an aqueous solution into an oily liquid to form a W/O emulsion in which the mRNA and the cell-free translational system are encapsulated in the phospholipid vesicle;

adding an oily liquid containing outer membrane lipids dissolved therein, to an aqueous phase to form a molecular membrane in which the lipids are arranged at the oil/water interface; and adding the W/O emulsion to the oil phase side of the interface and moving the W/O emulsion to the aqueous phase side of the interface such that the outer membrane lipid is added outside of the W/O emulsion to form a liposome.

5. A translation/expression regulation system comprising an mRNA according to claim 1.

6. The translation/expression regulation system according to claim 5, further comprising a microRNA complementary to the microRNA-binding site.

* * * * *

SEQUENCE LISTING

<160> NUMBER OF SEQ ID NOS: 59

<210> SEQ ID NO 1
<211> LENGTH: 720
<212> TYPE: DNA
<213> ORGANISM: Artificial Sequence
<220> FEATURE:
<223> OTHER INFORMATION: Synthetic Construct

<400> SEQUENCE: 1
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcgcc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 2
<211> LENGTH: 32
<212> TYPE: DNA
<213> ORGANISM: Artificial Sequence
<220> FEATURE:
<223> OTHER INFORMATION: Synthetic Construct

<400> SEQUENCE: 2
aaggagatat accaatggtg agcaagggcg ag 32

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
tattcattac ccggcggcgg tcacgaa 27

<210> SEQ ID NO 4
<211> LENGTH: 710
<212> TYPE: DNA
<213> ORGANISM: Artificial Sequence
<220> FEATURE:
<223> OTHER INFORMATION: Synthetic Construct

<400> SEQUENCE: 4
aaggagatat accaatggtg agcaagggcg aggagctgtt caccggggtg gtgcccatcc 60
tggtcgagct ggacggcgac gtaaacggcc acaagttcag cgtgtccggc gagggcgagg 120
gcgatgccac ctacggcaag ctgaccctga agttcatctg caccaccggc aagctgcccg 180
tgccctggcc caccctcgtg accaccctga cctacggcgt gcagtgcttc agccgctacc 240

```
ccgaccacat gaagcagcac gacttcttca agtccgccat gcccgaaggc tacgtccagg    300

agcgcaccat cttcttcaag gacgacggca actacaagac ccgcgccgag gtgaagttcg    360

agggcgacac cctggtgaac cgcatcgagc tgaagggcat cgacttcaag gaggacggca    420

acatcctggg gcacaagctg gagtacaact acaacagcca caacgtctat atcatggccg    480

acaagcagaa gaacggcatc aaggtgaact tcaagatccg ccacaacatc gaggacggca    540

gcgtgcagct cgccgaccac taccagcaga acacccccat cgccgacggc cccgtgctgc    600

tgcccgacaa ccactacctg agcacccagt ccgccctgag caaagacccc aacgagaagc    660

gcgatcacat ggtcctgctg gagttcgtga ccgccgccgg gtaatgaata                710
```

```
<210> SEQ ID NO 5
<211> LENGTH: 85
<212> TYPE: DNA
<213> ORGANISM: Artificial Sequence
<220> FEATURE:
<223> OTHER INFORMATION: Synthetic Construct

<400> SEQUENCE: 5

gaaattaata cgactcacta tagggagacc acaacggttt ccctctagaa ataattttgt     60

ttaactttaa gaaggagata tacca                                           85
```

```
<210> SEQ ID NO 6
<211> LENGTH: 781
<212> TYPE: DNA
<213> ORGANISM: Artificial Sequence
<220> FEATURE:
<223> OTHER INFORMATION: Synthetic Construct

<400> SEQUENCE: 6

gaaattaata cgactcacta tagggagacc acaacggttt ccctctagaa ataattttgt     60

ttaactttaa gaaggagata taccaatggt gagcaagggc gaggagctgt tcaccggggt    120

ggtgcccatc ctggtcgagc tggacggcga cgtaaacggc cacaagttca gcgtgtccgg    180

cgagggcgag ggcgatgcca cctacggcaa gctgaccctg aagttcatct gcaccaccgg    240

caagctgccc gtgccctggc ccaccctcgt gaccaccctg acctacggcg tgcagtgctt    300

cagccgctac cccgaccaca tgaagcagca cgacttcttc aagtccgcca tgcccgaagg    360

ctacgtccag gagcgcacca tcttcttcaa ggacgacggc aactacaaga cccgcgccga    420

ggtgaagttc gagggcgaca ccctggtgaa ccgcatcgag ctgaagggca tcgacttcaa    480

ggaggacggc aacatcctgg ggcacaagct ggagtacaac tacaacagcc acaacgtcta    540

tatcatggcc gacaagcaga agaacggcat caaggtgaac ttcaagatcc gccacaacat    600

cgaggacggc agcgtgcagc tcgccgacca ctaccagcag aacaccccca tcgccgacgg    660

ccccgtgctg ctgcccgaca accactacct gagcacccag tccgccctga gcaaagaccc    720

caacgagaag cgcgatcaca tggtcctgct ggagttcgtg accgccgccg ggtaatgaat    780

a                                                                    781
```

```
<210> SEQ ID NO 7
<211> LENGTH: 759
<212> TYPE: RNA
<213> ORGANISM: Artificial Sequence
<220> FEATURE:
<223> OTHER INFORMATION: Synthetic Construct

<400> SEQUENCE: 7

gggagaccac aacgguuucc cucuagaaau aauuuuguuu aacuuuaaga aggagauaua     60
```

```
ccaauggu ga gcaagggcga ggagcuguuc accggggugg ugcccauccu ggucgagcug    120

gacggcgacg uaaacggcca caaguucagc guguccggcg agggcgaggg cgaugccacc    180

uacggcaagc ugacccugaa guucaucugc accaccggca agcugcccgu gcccuggccc    240

acccucguga ccacccugac cuacggcgug cagugcuuca gccgcuaccc cgaccacaug    300

aagcagcacg acuucuucaa guccgccaug cccgaaggcu acguccagga gcgcaccauc    360

uucuucaagg acgacggcaa cuacaagacc cgcgccgagg ugaaguucga gggcgacacc    420

cuggugaacc gcaucgagcu gaagggcauc gacuucaagg aggacggcaa cauccugggg    480

cacaagcugg aguacaacua caacagccac aacgucuaua ucauggccga caagcagaag    540

aacggcauca aggugaacuu caagauccgc cacaacaucg aggacggcag cgugcagcuc    600

gccgaccacu accagcagaa cacccccauc gccgacggcc ccgugcugcu gcccgacaac    660

cacuaccuga gcacccaguc cgcccugagc aaagacccca acgagaagcg cgaucacaug    720

guccugcugg aguucgugac cgccgccggg uaaugaaua                            759
```

<210> SEQ ID NO 8
<211> LENGTH: 71
<212> TYPE: DNA
<213> ORGANISM: Artificial Sequence
<220> FEATURE:
<223> OTHER INFORMATION: Synthetic Construct

<400> SEQUENCE: 8

```
gggagaccac aacggtttcc ctctatctcc ttgcacgtgc cctgcttctc caagaaggag     60

atataccaat g                                                           71
```

<210> SEQ ID NO 9
<211> LENGTH: 764
<212> TYPE: DNA
<213> ORGANISM: Artificial Sequence
<220> FEATURE:
<223> OTHER INFORMATION: Synthetic Construct

<400> SEQUENCE: 9

```
gggagaccac aacggtttcc ctctatctcc ttgcacgtgc cctgcttctc caagaaggag     60

atataccaat ggtgagcaag ggcgaggagc tgttcaccgg ggtggtgccc atcctggtcg    120

agctggacgg cgacgtaaac ggccacaagt tcagcgtgtc cggcgagggc gagggcgatg    180

ccacctacgg caagctgacc ctgaagttca tctgcaccac cggcaagctg cccgtgccct    240

ggcccaccct cgtgaccacc ctgacctacg gcgtgcagtg cttcagccgc taccccgacc    300

acatgaagca gcacgacttc ttcaagtccg ccatgcccga aggctacgtc caggagcgca    360

ccatcttctt caaggacgac ggcaactaca agacccgcgc cgaggtgaag ttcgagggcg    420

acaccctggt gaaccgcatc gagctgaagg gcatcgactt caaggaggac ggcaacatcc    480

tggggcacaa gctggagtac aactacaaca gccacaacgt ctatatcatg gccgacaagc    540

agaagaacgg catcaaggtg aacttcaaga tccgccacaa catcgaggac ggcagcgtgc    600

agctcgccga ccactaccag cagaacaccc ccatcgccga cggccccgtg ctgctgcccg    660

acaaccacta cctgagcacc cagtccgccc tgagcaaaga ccccaacgag aagcgcgatc    720

acatggtcct gctggagttc gtgaccgccg ccgggtaatg aata                     764
```

<210> SEQ ID NO 10
<211> LENGTH: 42
<212> TYPE: DNA
<213> ORGANISM: Artificial Sequence
<220> FEATURE:

<223> OTHER INFORMATION: Synthetic Construct

<400> SEQUENCE: 10
gaaattaata cgactcacta tagggagacc acaacggttt cc 42

<210> SEQ ID NO 11
<211> LENGTH: 786
<212> TYPE: DNA
<213> ORGANISM: Artificial Sequence
<220> FEATURE:
<223> OTHER INFORMATION: Synthetic Construct

<400> SEQUENCE: 11
gaaattaata cgactcacta tagggagacc acaacggttt ccctctatct ccttgcacgt 60
gccctgcttc tccaagaagg agatatacca atggtgagca agggcgagga gctgttcacc 120
ggggtggtgc ccatcctggt cgagctggac ggcgacgtaa acggccacaa gttcagcgtg 180
tccggcgagg gcgagggcga tgccacctac ggcaagctga ccctgaagtt catctgcacc 240
accggcaagc tgcccgtgcc ctggcccacc ctcgtgacca ccctgaccta cggcgtgcag 300
tgcttcagcc gctaccccga ccacatgaag cagcacgact tcttcaagtc cgccatgccc 360
gaaggctacg tccaggagcg caccatcttc ttcaaggacg acggcaacta caagacccgc 420
gccgaggtga agttcgaggg cgacaccctg gtgaaccgca tcgagctgaa gggcatcgac 480
ttcaaggagg acggcaacat cctggggcac aagctggagt acaactacaa cagccacaac 540
gtctatatca tggccgacaa gcagaagaac ggcatcaagg tgaacttcaa gatccgccac 600
aacatcgagg acggcagcgt gcagctcgcc gaccactacc agcagaacac ccccatcgcc 660
gacggccccg tgctgctgcc cgacaaccac tacctgagca cccagtccgc cctgagcaaa 720
gaccccaacg agaagcgcga tcacatggtc ctgctggagt tcgtgaccgc cgccgggtaa 780
tgaata 786

<210> SEQ ID NO 12
<211> LENGTH: 764
<212> TYPE: RNA
<213> ORGANISM: Artificial Sequence
<220> FEATURE:
<223> OTHER INFORMATION: Synthetic Construct

<400> SEQUENCE: 12
gggagaccac aacgguuucc cucuaucucc uugcacgugc ccugcuucuc caagaaggag 60
auauaccaau ggugagcaag ggcgaggagc uguucaccgg gguggugccc auccuggucg 120
agcuggacgg cgacguaaac ggccacaagu ucagcguguc cggcgagggc gagggcgaug 180
ccaccuacgg caagcugacc cugaaguuca ucugcaccac cggcaagcug cccgugcccu 240
ggcccacccu cgugaccacc cugaccuacg gcgugcagug cuucagccgc uaccccgacc 300
acaugaagca gcacgacuuc uucaaguccg ccaugcccga aggcuacguc caggagcgca 360
ccaucuucuu caaggacgac ggcaacuaca agacccgcgc cgaggugaag uucgagggcg 420
acacccuggu gaaccgcauc gagcugaagg gcaucgacuu caaggaggac ggcaacaucc 480
uggggcacaa gcuggaguac aacuacaaca gccacaacgu cuauaucaug gccgacaagc 540
agaagaacgg caucaaggug aacuucaaga uccgccacaa caucgaggac ggcagcgugc 600
agcucgccga ccacuaccag cagaacaccc ccaucgccga cggccccgug cugcugcccg 660
acaaccacua ccugagcacc caguccgccc ugagcaaaga ccccaacgag aagcgcgauc 720
acaugguccu gcuggaguuc gugaccgccg ccggguaaug aaua 764

<210> SEQ ID NO 13
<211> LENGTH: 678
<212> TYPE: DNA
<213> ORGANISM: Artificial Sequence
<220> FEATURE:
<223> OTHER INFORMATION: Synthetic Construct

<400> SEQUENCE: 13

```
atggacaaca ccgaggacgt catcaaggag ttcatgcagt tcaaggtgcg catggagggc     60

tccgtgaacg gccactactt cgagatcgag ggcgagggcg agggcaagcc ctacgagggc    120

acccagaccg ccaagctgca ggtgaccaag ggcggccccc tgcccttcgc ctgggacatc    180

ctgtccccccc agttccagta cggctccaag gcctacgtga agcaccccgc cgacatcccc   240

gactacatga agctgtcctt ccccgagggc ttcacctggg agcgctccat gaacttcgag    300

gacggcggcg tggtggaggt gcagcaggac tcctccctgc aggacggcac cttcatctac    360

aaggtgaagt tcaagggcgt gaacttcccc gccgacggcc ccgtaatgca gaagaagact    420

gccggctggg agccctccac cgagaagctg tacccccagg acggcgtgct gaagggcgag    480

atctcccacg ccctgaagct gaaggacggc ggccactaca cctgcgactt caagaccgtg    540

tacaaggcca agaagcccgt gcagctgccc ggcaaccact acgtggactc caagctggac    600

atcaccaacc acaacgagga ctacaccgtg gtggagcagt acgagcacgc cgaggcccgc    660

cactccggct cccagtag                                                  678
```

<210> SEQ ID NO 14
<211> LENGTH: 33
<212> TYPE: DNA
<213> ORGANISM: Artificial Sequence
<220> FEATURE:
<223> OTHER INFORMATION: Synthetic Construct

<400> SEQUENCE: 14

```
aaggagatat accaatggac aacaccgagg acg                                  33
```

<210> SEQ ID NO 15
<211> LENGTH: 28
<212> TYPE: DNA
<213> ORGANISM: Artificial Sequence
<220> FEATURE:
<223> OTHER INFORMATION: Synthetic Construct

<400> SEQUENCE: 15

```
tattcattac tactgggagc cggagtgg                                        28
```

<210> SEQ ID NO 16
<211> LENGTH: 701
<212> TYPE: DNA
<213> ORGANISM: Artificial Sequence
<220> FEATURE:
<223> OTHER INFORMATION: Synthetic Construct

<400> SEQUENCE: 16

```
aaggagatat accaatggac aacaccgagg acgtcatcaa ggagttcatg cagttcaagg     60

tgcgcatgga gggctccgtg aacggccact acttcgagat cgagggcgag ggcgagggca    120

agccctacga gggcacccag accgccaagc tgcaggtgac caagggcggc cccctgccct    180

tcgcctggga catcctgtcc ccccagttcc agtacggctc caaggcctac gtgaagcacc    240

ccgccgacat ccccgactac atgaagctgt ccttccccga gggcttcacc tgggagcgct    300

ccatgaactt cgaggacggc ggcgtggtgg aggtgcagca ggactcctcc ctgcaggacg    360
```

```
gcaccttcat ctacaaggtg aagttcaagg gcgtgaactt ccccgccgac ggccccgtaa    420

tgcagaagaa gactgccggc tgggagccct ccaccgagaa gctgtacccc caggacggcg    480

tgctgaaggg cgagatctcc cacgccctga agctgaagga cggcggccac tacacctgcg    540

acttcaagac cgtgtacaag gccaagaagc ccgtgcagct gcccggcaac cactacgtgg    600

actccaagct ggacatcacc aaccacaacg aggactacac cgtggtggag cagtacgagc    660

acgccgaggc ccgccactcc ggctcccagt agtaatgaat a                        701
```

<210> SEQ ID NO 17
<211> LENGTH: 755
<212> TYPE: DNA
<213> ORGANISM: Artificial Sequence
<220> FEATURE:
<223> OTHER INFORMATION: Synthetic Construct

<400> SEQUENCE: 17

```
gggagaccac aacggtttcc ctctatctcc ttgcacgtgc cctgcttctc caagaaggag     60

atataccaat ggacaacacc gaggacgtca tcaaggagtt catgcagttc aaggtgcgca    120

tggagggctc cgtgaacggc cactacttcg agatcgaggg cgagggcgag ggcaagccct    180

acgagggcac ccagaccgcc aagctgcagg tgaccaaggg cggccccctg cccttcgcct    240

gggacatcct gtcccccag ttccagtacg gctccaaggc ctacgtgaag caccccgccg    300

acatccccga ctacatgaag ctgtccttcc ccgagggctt cacctgggag cgctccatga    360

acttcgagga cggcggcgtg gtggaggtgc agcaggactc ctccctgcag gacggcacct    420

tcatctacaa ggtgaagttc aagggcgtga acttccccgc cgacggcccc gtaatgcaga    480

agaagactgc cggctgggag ccctccaccg agaagctgta cccccaggac ggcgtgctga    540

agggcgagat ctcccacgcc ctgaagctga aggacggcgg ccactacacc tgcgacttca    600

agaccgtgta caaggccaag aagcccgtgc agctgcccgg caaccactac gtggactcca    660

agctggacat caccaaccac aacgaggact acaccgtggt ggagcagtac gagcacgccg    720

aggcccgcca ctccggctcc cagtagtaat gaata                                755
```

<210> SEQ ID NO 18
<211> LENGTH: 777
<212> TYPE: DNA
<213> ORGANISM: Artificial Sequence
<220> FEATURE:
<223> OTHER INFORMATION: Synthetic Construct

<400> SEQUENCE: 18

```
gaaattaata cgactcacta tagggagacc acaacggttt ccctctatct ccttgcacgt     60

gccctgcttc tccaagaagg agatatacca atggacaaca ccgaggacgt catcaaggag    120

ttcatgcagt tcaaggtgcg catggagggc tccgtgaacg gccactactt cgagatcgag    180

ggcgagggcg agggcaagcc ctacgagggc acccagaccg ccaagctgca ggtgaccaag    240

ggcggccccc tgcccttcgc ctgggacatc ctgtcccccc agttccagta cggctccaag    300

gcctacgtga agcaccccgc cgacatcccc gactacatga agctgtcctt ccccgagggc    360

ttcacctggg agcgctccat gaacttcgag gacggcggcg tggtggaggt gcagcaggac    420

tcctccctgc aggacggcac cttcatctac aaggtgaagt tcaagggcgt gaacttcccc    480

gccgacggcc ccgtaatgca gaagaagact gccggctggg agccctccac cgagaagctg    540

tacccccagg acggcgtgct gaagggcgag atctcccacg ccctgaagct gaaggacggc    600

ggccactaca cctgcgactt caagaccgtg tacaaggcca agaagcccgt gcagctgccc    660
```

```
ggcaaccact acgtggactc caagctggac atcaccaacc acaacgagga ctacaccgtg    720

gtggagcagt acgagcacgc cgaggcccgc cactccggct cccagtagta atgaata       777


<210> SEQ ID NO 19
<211> LENGTH: 755
<212> TYPE: RNA
<213> ORGANISM: Artificial Sequence
<220> FEATURE:
<223> OTHER INFORMATION: Synthetic Construct

<400> SEQUENCE: 19

gggagaccac aacgguuucc cucuaucucc uugcacgugc ccugcuucuc caagaaggag     60

auauaccaau ggacaacacc gaggacguca ucaaggaguu caugcaguuc aaggugcgca    120

uggagggcuc cgugaacggc cacuacuucg agaucgaggg cgagggcgag ggcaagcccu    180

acgagggcac ccagaccgcc aagcugcagg ugaccaaggg cggcccccug cccuucgccu    240

gggacauccu gucccccag uuccaguacg gcuccaaggc cuacgugaag caccccgccg    300

acaucccga cuacaugaag cuguccuucc ccgagggcuu caccugggag cgcuccauga    360

acuucgagga cggcggcgug guggaggugc agcaggacuc cucccugcag gacggcaccu    420

ucaucuacaa ggugaaguuc aagggcguga acuuccccgc cgacggcccc guaaugcaga    480

agaagacugc cggcugggag cccuccaccg agaagcugua cccccaggac ggcgugcuga    540

agggcgagau cucccacgcc cugaagcuga aggacggcgg ccacuacacc ugcgacuuca    600

agaccgugua caaggccaag aagcccgugc agcugcccgg caaccacuac guggacucca    660

agcuggacau caccaaccac aacgaggacu acaccguggu ggagcaguac gagcacgccg    720

aggcccgcca cuccggcucc caguaguaau gaaua                               755


<210> SEQ ID NO 20
<211> LENGTH: 71
<212> TYPE: DNA
<213> ORGANISM: Artificial Sequence
<220> FEATURE:
<223> OTHER INFORMATION: Synthetic Construct

<400> SEQUENCE: 20

gggagaccac aacggtttcc ctctatctcc tgatattgac acggctcaat caagaaggag     60

atataccaat g                                                          71


<210> SEQ ID NO 21
<211> LENGTH: 764
<212> TYPE: DNA
<213> ORGANISM: Artificial Sequence
<220> FEATURE:
<223> OTHER INFORMATION: Synthetic Construct

<400> SEQUENCE: 21

gggagaccac aacggtttcc ctctatctcc tgatattgac acggctcaat caagaaggag     60

atataccaat ggtgagcaag ggcgaggagc tgttcaccgg ggtggtgccc atcctggtcg    120

agctggacgg cgacgtaaac ggccacaagt tcagcgtgtc cggcgagggc gagggcgatg    180

ccacctacgg caagctgacc ctgaagttca tctgcaccac cggcaagctg cccgtgccct    240

ggcccaccct cgtgaccacc ctgacctacg gcgtgcagtg cttcagccgc taccccgacc    300

acatgaagca gcacgacttc ttcaagtccg ccatgcccga aggctacgtc caggagcgca    360

ccatcttctt caaggacgac ggcaactaca agacccgcgc cgaggtgaag ttcgagggcg    420

acaccctggt gaaccgcatc gagctgaagg gcatcgactt caaggaggac ggcaacatcc    480
```

tggggcacaa gctggagtac aactacaaca gccacaacgt ctatatcatg gccgacaagc 540
agaagaacgg catcaaggtg aacttcaaga tccgccacaa catcgaggac ggcagcgtgc 600
agctcgccga ccactaccag cagaacaccc ccatcgccga cggccccgtg ctgctgcccg 660
acaaccacta cctgagcacc cagtccgccc tgagcaaaga ccccaacgag aagcgcgatc 720
acatggtcct gctggagttc gtgaccgccg ccgggtaatg aata 764

<210> SEQ ID NO 22
<211> LENGTH: 786
<212> TYPE: DNA
<213> ORGANISM: Artificial Sequence
<220> FEATURE:
<223> OTHER INFORMATION: Synthetic Construct

<400> SEQUENCE: 22
gaaattaata cgactcacta tagggagacc acaacggttt ccctctatct cctgatattg 60
acacggctca atcaagaagg agatatacca atggtgagca agggcgagga gctgttcacc 120
ggggtggtgc ccatcctggt cgagctggac ggcgacgtaa acggccacaa gttcagcgtg 180
tccggcgagg gcgagggcga tgccacctac ggcaagctga ccctgaagtt catctgcacc 240
accggcaagc tgcccgtgcc ctggcccacc ctcgtgacca ccctgaccta cggcgtgcag 300
tgcttcagcc gctaccccga ccacatgaag cagcacgact tcttcaagtc cgccatgccc 360
gaaggctacg tccaggagcg caccatcttc ttcaaggacg acggcaacta caagacccgc 420
gccgaggtga agttcgaggg cgacaccctg gtgaaccgca tcgagctgaa gggcatcgac 480
ttcaaggagg acggcaacat cctggggcac aagctggagt acaactacaa cagccacaac 540
gtctatatca tggccgacaa gcagaagaac ggcatcaagg tgaacttcaa gatccgccac 600
aacatcgagg acggcagcgt gcagctcgcc gaccactacc agcagaacac ccccatcgcc 660
gacggccccg tgctgctgcc cgacaaccac tacctgagca cccagtccgc cctgagcaaa 720
gaccccaacg agaagcgcga tcacatggtc ctgctggagt tcgtgaccgc cgccgggtaa 780
tgaata 786

<210> SEQ ID NO 23
<211> LENGTH: 764
<212> TYPE: RNA
<213> ORGANISM: Artificial Sequence
<220> FEATURE:
<223> OTHER INFORMATION: Synthetic Construct

<400> SEQUENCE: 23
gggagaccac aacgguuucc cucuaucucc ugauauugac acggcucaau caagaaggag 60
auauaccaau ggugagcaag ggcgaggagc uguucaccgg gguggugccc auccuggucg 120
agcuggacgg cgacguaaac ggccacaagu ucagcguguc cggcgagggc gagggcgaug 180
ccaccuacgg caagcugacc cugaaguuca ucugcaccac cggcaagcug cccgugcccu 240
ggcccacccu cgugaccacc cugaccuacg gcgugcagug cuucagccgc uaccccgacc 300
acaugaagca gcacgacuuc uucaaguccg ccaugcccga aggcuacguc caggagcgca 360
ccaucuucuu caaggacgac ggcaacuaca agacccgcgc cgaggugaag uucgagggcg 420
acacccuggu gaaccgcauc gagcugaagg gcaucgacuu caaggaggac ggcaacaucc 480
uggggcacaa gcuggaguac aacuacaaca gccacaacgu cuauaucaug gccgacaagc 540
agaagaacgg caucaaggug aacuucaaga uccgccacaa caucgaggac ggcagcgugc 600
agcucgccga ccacuaccag cagaacaccc ccaucgccga cggccccgug cugcugcccg 660
acaaccacua ccugagcacc caguccgccc ugagcaaaga ccccaacgag aagcgcgauc 720
acaugguccu gcuggaguuc gugaccgccg ccggguaaug aaua 764

<210> SEQ ID NO 24
<211> LENGTH: 71
<212> TYPE: DNA
<213> ORGANISM: Artificial Sequence
<220> FEATURE:
<223> OTHER INFORMATION: Synthetic Construct

<400> SEQUENCE: 24
gggagaccac aacggtttcc ctctatctcc tgatattggc gcggctcaat caagaaggag 60
atataccaat g 71

<210> SEQ ID NO 25
<211> LENGTH: 764
<212> TYPE: DNA
<213> ORGANISM: Artificial Sequence
<220> FEATURE:
<223> OTHER INFORMATION: Synthetic Construct

<400> SEQUENCE: 25
gggagaccac aacggtttcc ctctatctcc tgatattggc gcggctcaat caagaaggag 60
atataccaat ggtgagcaag ggcgaggagc tgttcaccgg ggtggtgccc atcctggtcg 120
agctggacgg cgacgtaaac ggccacaagt tcagcgtgtc cggcgagggc gagggcgatg 180
ccacctacgg caagctgacc ctgaagttca tctgcaccac cggcaagctg cccgtgccct 240
ggcccaccct cgtgaccacc ctgacctacg gcgtgcagtg cttcagccgc taccccgacc 300
acatgaagca gcacgacttc ttcaagtccg ccatgcccga aggctacgtc caggagcgca 360
ccatcttctt caaggacgac ggcaactaca agacccgcgc cgaggtgaag ttcgagggcg 420
acaccctggt gaaccgcatc gagctgaagg gcatcgactt caaggaggac ggcaacatcc 480
tggggcacaa gctggagtac aactacaaca gccacaacgt ctatatcatg gccgacaagc 540
agaagaacgg catcaaggtg aacttcaaga tccgccacaa catcgaggac ggcagcgtgc 600
agctcgccga ccactaccag cagaacaccc ccatcgccga cggccccgtg ctgctgcccg 660
acaaccacta cctgagcacc cagtccgccc tgagcaaaga ccccaacgag aagcgcgatc 720
acatggtcct gctggagttc gtgaccgccg ccgggtaatg aata 764

<210> SEQ ID NO 26
<211> LENGTH: 786
<212> TYPE: DNA
<213> ORGANISM: Artificial Sequence
<220> FEATURE:
<223> OTHER INFORMATION: Synthetic Construct

<400> SEQUENCE: 26
gaaattaata cgactcacta tagggagacc acaacggttt ccctctatct cctgatattg 60
gcgcggctca atcaagaagg agatatacca atggtgagca agggcgagga gctgttcacc 120
ggggtggtgc ccatcctggt cgagctggac ggcgacgtaa acggccacaa gttcagcgtg 180
tccggcgagg gcgagggcga tgccacctac ggcaagctga ccctgaagtt catctgcacc 240
accggcaagc tgcccgtgcc ctggcccacc ctcgtgacca ccctgaccta cggcgtgcag 300
tgcttcagcc gctaccccga ccacatgaag cagcacgact tcttcaagtc cgccatgccc 360
gaaggctacg tccaggagcg caccatcttc ttcaaggacg acggcaacta caagacccgc 420
gccgaggtga agttcgaggg cgacaccctg gtgaaccgca tcgagctgaa gggcatcgac 480

```
ttcaaggagg acggcaacat cctggggcac aagctggagt acaactacaa cagccacaac    540

gtctatatca tggccgacaa gcagaagaac ggcatcaagg tgaacttcaa gatccgccac    600

aacatcgagg acggcagcgt gcagctcgcc gaccactacc agcagaacac ccccatcgcc    660

gacggccccg tgctgctgcc cgacaaccac tacctgagca cccagtccgc cctgagcaaa    720

gaccccaacg agaagcgcga tcacatggtc ctgctggagt tcgtgaccgc cgccgggtaa    780

tgaata                                                               786
```

<210> SEQ ID NO 27
<211> LENGTH: 764
<212> TYPE: RNA
<213> ORGANISM: Artificial Sequence
<220> FEATURE:
<223> OTHER INFORMATION: Synthetic Construct

<400> SEQUENCE: 27

```
gggagaccac aacgguuucc cucuaucucc ugauauuggc gcggcucaau caagaaggag     60

auauaccaau ggugagcaag ggcgaggagc uguucaccgg gguggugccc auccuggucg    120

agcuggacgg cgacguaaac ggccacaagu ucagcguguc cggcgagggc gagggcgaug    180

ccaccuacgg caagcugacc cugaaguuca ucugcaccac cggcaagcug cccgugcccu    240

ggcccacccu cgugaccacc cugaccuacg gcgugcagug cuucagccgc uaccccgacc    300

acaugaagca gcacgacuuc uucaaguccg ccaugcccga aggcuacguc caggagcgca    360

ccaucuucuu caaggacgac ggcaacuaca agacccgcgc cgaggugaag uucgagggcg    420

acacccuggu gaaccgcauc gagcugaagg gcaucgacuu caaggaggac ggcaacaucc    480

uggggcacaa gcuggaguac aacuacaaca gccacaacgu cuauaucaug gccgacaagc    540

agaagaacgg caucaaggug aacuucaaga uccgccacaa caucgaggac ggcagcgugc    600

agcucgccga ccacuaccag cagaacaccc ccaucgccga cggccccgug cugcugcccg    660

acaaccacua ccugagcacc caguccgccc ugagcaaaga ccccaacgag aagcgcgauc    720

acaugguccu gcuggaguuc gugaccgccg ccggguaaug aaua                     764
```

<210> SEQ ID NO 28
<211> LENGTH: 24
<212> TYPE: RNA
<213> ORGANISM: Artificial Sequence
<220> FEATURE:
<223> OTHER INFORMATION: Synthetic Construct

<400> SEQUENCE: 28

```
uugaagagga cuuggaacuu cgau                                            24
```

<210> SEQ ID NO 29
<211> LENGTH: 21
<212> TYPE: RNA
<213> ORGANISM: Artificial Sequence
<220> FEATURE:
<223> OTHER INFORMATION: Synthetic Construct

<400> SEQUENCE: 29

```
uggagaagca gggcacgugc a                                               21
```

<210> SEQ ID NO 30
<211> LENGTH: 21
<212> TYPE: RNA
<213> ORGANISM: Artificial Sequence
<220> FEATURE:
<223> OTHER INFORMATION: Synthetic Construct

<400> SEQUENCE: 30
ugauugagcc gugucaauau c 21

<210> SEQ ID NO 31
<211> LENGTH: 21
<212> TYPE: RNA
<213> ORGANISM: Artificial Sequence
<220> FEATURE:
<223> OTHER INFORMATION: Synthetic Construct

<400> SEQUENCE: 31
ugauugagcc gcgccaauau c 21

<210> SEQ ID NO 32
<211> LENGTH: 763
<212> TYPE: RNA
<213> ORGANISM: Artificial Sequence
<220> FEATURE:
<223> OTHER INFORMATION: Synthetic Construct

<400> SEQUENCE: 32
gggagaccac aacgguuucc cucuaucucc ugugcucacu cucuucuguc aagaaggaga 60
uauaccaaug gugagcaagg gcgaggagcu guucaccggg guggugccca uccuggucga 120
gcuggacggc gacguaaacg gccacaaguu cagcgugucc ggcgagggcg agggcgaugc 180
caccuacggc aagcugaccc ugaaguucau cugcaccacc ggcaagcugc ccgugcccug 240
gcccacccuc gugaccaccc ugaccuacgg cgugcagugc uucagccgcu accccgacca 300
caugaagcag cacgacuucu ucaaguccgc caugcccgaa ggcuacgucc aggagcgcac 360
caucuucuuc aaggacgacg gcaacuacaa gacccgcgcc gaggugaagu ucgagggcga 420
cacccuggug aaccgcaucg agcugaaggg caucgacuuc aaggaggacg gcaacauccu 480
ggggcacaag cuggaguaca acuacaacag ccacaacguc uauaucaugg ccgacaagca 540
gaagaacggc aucaagguga acuucaagau ccgccacaac aucgaggacg gcagcgugca 600
gcucgccgac cacuaccagc agaacacccc caucgccgac ggccccgugc ugcugcccga 660
caaccacuac cugagcaccc aguccgcccu gagcaaagac cccaacgaga agcgcgauca 720 cauggucug cuggaguucg ugaccgccgc cggguaauga aua 763

<210> SEQ ID NO 33
<211> LENGTH: 70
<212> TYPE: DNA
<213> ORGANISM: Artificial Sequence
<220> FEATURE:
<223> OTHER INFORMATION: Synthetic Construct

<400> SEQUENCE: 33
gggagaccac aacggtttcc ctctatctcc tgtgctcact ctcttctgtc aagaaggaga 60
tataccaatg 70

<210> SEQ ID NO 34
<211> LENGTH: 754
<212> TYPE: RNA
<213> ORGANISM: Artificial Sequence
<220> FEATURE:
<223> OTHER INFORMATION: Synthetic Construct

<400> SEQUENCE: 34
gggagaccac aacgguuucc cucuaucucc ugugcucacu cucuucuguc aagaaggaga 60
uauaccaaug gacaacaccg aggacgucau caaggaguuc augcaguuca aggugcgcau 120

```
ggagggcucc gugaacggcc acuacuucga gaucgagggc gagggcgagg gcaagcccua    180

cgagggcacc cagaccgcca agcugcaggu gaccaagggc ggccccccugc ccuucgccug    240

ggacauccug uccccccagu uccaguacgg cuccaaggcc uacgugaagc accccgccga    300

cauccccgac uacaugaagc uguccuuccc cgagggcuuc accugggagc gcuccaugaa    360

cuucgaggac ggcggcgugg uggaggugca gcaggacucc ucccugcagg acggcaccuu    420

caucuacaag gugaaguuca agggcgugaa cuuccccgcc gacggccccg uaaugcagaa    480

gaagacugcc ggcugggagc ccuccaccga gaagcuguac cccccaggacg gcgugcugaa    540

gggcgagauc ucccacgccc ugaagcugaa ggacggcggc cacuacaccu gcgacuucaa    600

gaccguguac aaggccaaga agcccgugca gcugcccggc aaccacuacg uggacuccaa    660

gcuggacauc accaaccaca acgaggacua caccguggug gagcaguacg agcacgccga    720

ggcccgccac uccggcuccc aguaguaaug aaua                                754
```

<210> SEQ ID NO 35
<211> LENGTH: 20
<212> TYPE: RNA
<213> ORGANISM: Artificial Sequence
<220> FEATURE:
<223> OTHER INFORMATION: Synthetic Construct

<400> SEQUENCE: 35

```
ugacagaaga gagugagcac                                                 20
```

<210> SEQ ID NO 36
<211> LENGTH: 780
<212> TYPE: RNA
<213> ORGANISM: Artificial Sequence
<220> FEATURE:
<223> OTHER INFORMATION: Synthetic Construct

<400> SEQUENCE: 36

```
gggagaccac aacgguuucc cucuagaaau aauuuuguuu aacuuuaaga aggagauaua     60

ccaauggugc ucacucucuu cugucaggug agcaagggcg aggagcuguu caccggggug    120

gugcccaucc uggucgagcu ggacggcgac guaaacggcc acaaguucag cguguccggc    180

gagggcgagg gcgaugccac cuacggcaag cugacccuga aguucaucug caccaccggc    240

aagcugcccg ugcccuggcc cacccucgug accacccuga ccuacggcgu gcagugcuuc    300

agccgcuacc ccgaccacau gaagcagcac gacuucuuca aguccgccau gcccgaaggc    360

uacguccagg agcgcaccau cuucuucaag gacgacggca acuacaagac ccgcgccgag    420

gugaaguucg agggcgacac ccuggugaac cgcaucgagc ugaagggcau cgacuucaag    480

gaggacggca acauccuggg gcacaagcug gaguacaacu acaacagcca caacgucuau    540

aucauggccg acaagcagaa gaacggcauc aaggugaacu ucaagauccg ccacaacauc    600

gaggacggca gcgugcagcu cgccgaccac uaccagcaga acacccccau cgccgacggc    660

cccgugcugc ugcccgacaa ccacuaccug agcacccagu ccgcccugag caaagacccc    720

aacgagaagc gcgaucacau gguccugcug gaguucguga ccgccgccgg guaaugaaua    780
```

<210> SEQ ID NO 37
<211> LENGTH: 20
<212> TYPE: RNA
<213> ORGANISM: Artificial Sequence
<220> FEATURE:
<223> OTHER INFORMATION: Synthetic Construct

<400> SEQUENCE: 37
gugcucacuc ucuucuguca 20

<210> SEQ ID NO 38
<211> LENGTH: 780
<212> TYPE: RNA
<213> ORGANISM: Artificial Sequence
<220> FEATURE:
<223> OTHER INFORMATION: Synthetic Construct

<400> SEQUENCE: 38
gggagaccac aacgguuucc cucuagaaau aauuuuguuu aacuuuaaga aggagauaua 60
ccaaugugca cgugcccugc uucuccagug agcaagggcg aggagcuguu caccggggug 120
gugcccaucc uggucgagcu ggacggcgac guaaacggcc acaaguucag cguguccggc 180
gagggcgagg gcgaugccac cuacggcaag cugacccuga aguucaucug caccaccggc 240
aagcugcccg ugcccuggcc cacccucgug accacccuga ccuacggcgu gcagugcuuc 300
agccgcuacc ccgaccacau gaagcagcac gacuucuuca aguccgccau gcccgaaggc 360
uacguccagg agcgcaccau cuucuucaag gacgacggca acuacaagac ccgcgccgag 420
gugaaguucg agggcgacac ccuggugaac cgcaucgagc ugaagggcau cgacuucaag 480
gaggacggca acauccuggg gcacaagcug gaguacaacu acaacagcca caacgucuau 540
aucauggccg acaagcagaa gaacggcauc aaggugaacu ucaagauccg ccacaacauc 600
gaggacggca gcgugcagcu cgccgaccac uaccagcaga acacccccau cgccgacggc 660
cccgugcugc ugcccgacaa ccacuaccug agcacccagu ccgcccugag caaagacccc 720
aacgagaagc gcgaucacau gguccugcug gaguucguga ccgccgccgg guaaugaaua 780

<210> SEQ ID NO 39
<211> LENGTH: 21
<212> TYPE: RNA
<213> ORGANISM: Artificial Sequence
<220> FEATURE:
<223> OTHER INFORMATION: Synthetic Construct

<400> SEQUENCE: 39
ugcacgugcc cugcuucucc a 21

<210> SEQ ID NO 40
<211> LENGTH: 56
<212> TYPE: DNA
<213> ORGANISM: Artificial Sequence
<220> FEATURE:
<223> OTHER INFORMATION: Synthetic Construct

<400> SEQUENCE: 40
aaggagatat accaatggtg ctcactctct tctgtcaggt gagcaagggc gaggag 56

<210> SEQ ID NO 41
<211> LENGTH: 56
<212> TYPE: DNA
<213> ORGANISM: Artificial Sequence
<220> FEATURE:
<223> OTHER INFORMATION: Synthetic Construct

<400> SEQUENCE: 41
aaggagatat accaatgtgc acgtgccctg cttctccagt gagcaagggc gaggag 56

<210> SEQ ID NO 42
<211> LENGTH: 771
<212> TYPE: RNA
<213> ORGANISM: Artificial Sequence
<220> FEATURE:

<223> OTHER INFORMATION: Synthetic Construct

<400> SEQUENCE: 42

```
gggagaccac aacgguuucc cucuagaaau aauuuuguuu aacuuuaaga aggagauaua     60

ccaauggugc ucacucucuu cugucaggac aacaccgagg acgucaucaa ggaguucaug    120

caguucaagg ugcgcaugga gggcuccgug aacggccacu acuucgagau cgagggcgag    180

ggcgagggca agcccuacga gggcacccag accgccaagc ugcaggugac caagggcggc    240

ccccugcccu ucgccuggga cauccugucc ccccaguucc aguacggcuc caaggccuac    300

gugaagcacc ccgccgacau ccccgacuac augaagcugu ccuuccccga gggcuucacc    360

ugggagcgcu ccaugaacuu cgaggacggc ggcguggugg aggugcagca ggacuccucc    420

cugcaggacg gcaccuucau cuacaaggug aaguucaagg gcgugaacuu ccccgccgac    480

ggccccguaa ugcagaagaa gacugccggc ugggagcccu ccaccgagaa gcuguacccc    540

caggacggcg ugcugaaggg cgagaucucc cacgcccuga agcugaagga cggcggccac    600

uacaccugcg acuucaagac cguguacaag gccaagaagc ccgugcagcu gcccggcaac    660

cacuacgugg acuccaagcu ggacaucacc aaccacaacg aggacuacac cgugguggag    720

caguacgagc acgccgaggc ccgccacucc ggcucccagu aguaaugaau a             771
```

<210> SEQ ID NO 43
<211> LENGTH: 771
<212> TYPE: RNA
<213> ORGANISM: Artificial Sequence
<220> FEATURE:
<223> OTHER INFORMATION: Synthetic Construct

<400> SEQUENCE: 43

```
gggagaccac aacgguuucc cucuagaaau aauuuuguuu aacuuuaaga aggagauaua     60

ccaaugugca cgugcccugc uucuccagac aacaccgagg acgucaucaa ggaguucaug    120

caguucaagg ugcgcaugga gggcuccgug aacggccacu acuucgagau cgagggcgag    180

ggcgagggca agcccuacga gggcacccag accgccaagc ugcaggugac caagggcggc    240

ccccugcccu ucgccuggga cauccugucc ccccaguucc aguacggcuc caaggccuac    300

gugaagcacc ccgccgacau ccccgacuac augaagcugu ccuuccccga gggcuucacc    360

ugggagcgcu ccaugaacuu cgaggacggc ggcguggugg aggugcagca ggacuccucc    420

cugcaggacg gcaccuucau cuacaaggug aaguucaagg gcgugaacuu ccccgccgac    480

ggccccguaa ugcagaagaa gacugccggc ugggagcccu ccaccgagaa gcuguacccc    540

caggacggcg ugcugaaggg cgagaucucc cacgcccuga agcugaagga cggcggccac    600

uacaccugcg acuucaagac cguguacaag gccaagaagc ccgugcagcu gcccggcaac    660

cacuacgugg acuccaagcu ggacaucacc aaccacaacg aggacuacac cgugguggag    720

caguacgagc acgccgaggc ccgccacucc ggcucccagu aguaaugaau a             771
```

<210> SEQ ID NO 44
<211> LENGTH: 21
<212> TYPE: RNA
<213> ORGANISM: Artificial Sequence
<220> FEATURE:
<223> OTHER INFORMATION: Synthetic Construct

<400> SEQUENCE: 44

```
uuuggauuga agggagcucu a                                               21
```

<210> SEQ ID NO 45

<211> LENGTH: 21
<212> TYPE: RNA
<213> ORGANISM: Artificial Sequence
<220> FEATURE:
<223> OTHER INFORMATION: Synthetic Construct

<400> SEQUENCE: 45
uagagcuccc uucaauccaa a 21

<210> SEQ ID NO 46
<211> LENGTH: 796
<212> TYPE: RNA
<213> ORGANISM: Artificial Sequence
<220> FEATURE:
<223> OTHER INFORMATION: Synthetic Construct

<400> SEQUENCE: 46
gggagaccac aacgguuucc cuuagagcuc ccuucaaucc aaauaucucc uuagagcucc 60
cuucaaucca aaagaaggag auauaccaau ggaagggagc ucugugagca agggcgagga 120
gcuguucacc ggggugguge ccauccuggu cgagcuggac ggcgacguaa acggccacaa 180
guucagcgug uccggcgagg gcgagggcga ugccaccuac ggcaagcuga cccugaaguu 240
caucugcacc accggcaagc ugcccgugcc cuggcccacc cucgugacca cccugaccua 300
cggcgugcag ugcuucagcc gcuaccccga ccacaugaag cagcacgacu ucuucaaguc 360
cgccaugccc gaaggcuacg uccaggagcg caccaucuuc uucaaggacg acggcaacua 420
caagacccgc gccgagguga aguucgaggg cgacacccug gugaaccgca ucgagcugaa 480
gggcaucgac uucaaggagg acggcaacau ccuggggcac aagcuggagu acaacuacaa 540
cagccacaac gucuauauca uggccgacaa gcagaagaac ggcaucaagg ugaacuucaa 600
gauccgccac aacaucgagg acggcagcgu gcagcucgcc gaccacuacc agcagaacac 660
ccccaucgcc gacggccccg ugcugcugcc cgacaaccac uaccugagca cccaguccgc 720
ccugagcaaa gaccccaacg agaagcgcga ucacaugguc cugcuggagu ucgugaccgc 780
cgccggguaa ugaaua 796

<210> SEQ ID NO 47
<211> LENGTH: 24
<212> TYPE: RNA
<213> ORGANISM: Artificial Sequence
<220> FEATURE:
<223> OTHER INFORMATION: Synthetic Construct

<400> SEQUENCE: 47
aucgaaguuc caaguccucu ucaa 24

<210> SEQ ID NO 48
<211> LENGTH: 805
<212> TYPE: RNA
<213> ORGANISM: Artificial Sequence
<220> FEATURE:
<223> OTHER INFORMATION: Synthetic Construct

<400> SEQUENCE: 48
gggagaccac aacgguuucc cuaucgaagu uccaaguccu cuucaauauc uccuaucgaa 60
guuccaaguc cucuucaaag aaggagauau accaauggac uuggaacuuc gagugagcaa 120
gggcgaggag cuguucaccg ggguggugcc cauccugguc gagcuggacg gcgacguaaa 180
cggccacaag uucagcgugu ccggcgaggg cgagggcgau gccaccuacg gcaagcugac 240
ccugaaguuc aucugcacca ccggcaagcu gcccgugccc uggcccaccc ucgugaccac 300
ccugaccuac ggcgugcagu gcuucagccg cuaccccgac cacaugaagc agcacgacuu 360
cuucaagucc gccaugcccg aaggcuacgu ccaggagcgc accaucuucu ucaaggacga 420
cggcaacuac aagacccgcg ccgaggugaa guucgagggc gacacccugg ugaaccgcau 480
cgagcugaag ggcaucgacu ucaaggagga cggcaacauc cuggggcaca agcuggagua 540
caacuacaac agccacaacg ucuauaucau ggccgacaag cagaagaacg gcaucaaggu 600
gaacuucaag auccgccaca acaucgagga cggcagcgug cagcucgccg accacuacca 660
gcagaacacc cccaucgccg acggccccgu gcugcugccc gacaaccacu accugagcac 720
ccaguccgcc cugagcaaag accccaacga gaagcgcgau cacauggucc ugcuggaguu 780
cgugaccgcc gccggguaau gaaua 805

<210> SEQ ID NO 49
<211> LENGTH: 77
<212> TYPE: RNA
<213> ORGANISM: Artificial Sequence
<220> FEATURE:
<223> OTHER INFORMATION: Synthetic Construct

<400> SEQUENCE: 49
gggagaccac aacgguuucc cucuaucucc uugcacgugc ccugcuucuc caagaaggag 60
auauaccaau ggugagc 77

<210> SEQ ID NO 50
<211> LENGTH: 46
<212> TYPE: RNA
<213> ORGANISM: Artificial Sequence
<220> FEATURE:
<223> OTHER INFORMATION: Synthetic Construct

<400> SEQUENCE: 50
agaaggagau auaccaaugg ugcucacucu cuucugucag gugagc 46

<210> SEQ ID NO 51
<211> LENGTH: 7
<212> TYPE: PRT
<213> ORGANISM: Artificial Sequence
<220> FEATURE:
<223> OTHER INFORMATION: Synthetic Construct

<400> SEQUENCE: 51

Val Leu Thr Leu Phe Cys Glu
1               5

<210> SEQ ID NO 52
<211> LENGTH: 46
<212> TYPE: RNA
<213> ORGANISM: Artificial Sequence
<220> FEATURE:
<223> OTHER INFORMATION: Synthetic Construct

<400> SEQUENCE: 52
agaaggagau auaccaaugu gcacgugccc ugcuucucca gugagc 46

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Cys Thr Cys Pro Ala Ser Pro 1 5

<210> SEQ ID NO 54
<211> LENGTH: 52
<212> TYPE: RNA
<213> ORGANISM: Artificial Sequence
<220> FEATURE:
<223> OTHER INFORMATION: Synthetic Construct

<400> SEQUENCE: 54
agaaggagau auaccaaugg ugcucacucu cuucugucag gacaacaccg ag 52

<210> SEQ ID NO 55
<211> LENGTH: 52
<212> TYPE: RNA
<213> ORGANISM: Artificial Sequence
<220> FEATURE:
<223> OTHER INFORMATION: Synthetic Construct

<400> SEQUENCE: 55
agaaggagau auaccaaugu gcacgugccc ugcuucucca gacaacaccg ag 52

<210> SEQ ID NO 56
<211> LENGTH: 109
<212> TYPE: RNA
<213> ORGANISM: Artificial Sequence
<220> FEATURE:
<223> OTHER INFORMATION: Synthetic Construct

<400> SEQUENCE: 56
gggagaccac aacgguuucc cuuagagcuc ccuucaaucc aaauaucucc uuagagcucc 60
cuucaaucca aaagaaggag auauaccaau ggaagggagc ucugugagc 109

<210> SEQ ID NO 57
<211> LENGTH: 4
<212> TYPE: PRT
<213> ORGANISM: Artificial Sequence
<220> FEATURE:
<223> OTHER INFORMATION: Synthetic Construct

<400> SEQUENCE: 57

Glu Gly Ser Ser
1

<210> SEQ ID NO 58
<211> LENGTH: 118
<212> TYPE: RNA
<213> ORGANISM: Artificial Sequence
<220> FEATURE:
<223> OTHER INFORMATION: Synthetic Construct

<400> SEQUENCE: 58
gggagaccac aacgguuucc cuaucgaagu uccaaguccu cuucaauauc uccuaucgaa 60
guuccaaguc cucuucaaag aaggagauau accaauggac uuggaacuuc gagugagc 118

<210> SEQ ID NO 59
<211> LENGTH: 5
<212> TYPE: PRT
<213> ORGANISM: Artificial Sequence
<220> FEATURE:
<223> OTHER INFORMATION: Synthetic Construct

<400> SEQUENCE: 59

Asp Leu Glu Leu Arg
1 5